United States Patent
Cork et al.

(10) Patent No.: US 6,256,643 B1
(45) Date of Patent: Jul. 3, 2001

(54) SYSTEMS AND METHODS FOR STORING, RETRIEVING, AND MANIPULATING DATA IN MEDICAL PROCESSING DEVICES

(75) Inventors: William H Cork, Lake Bluff; Mark Weber, Algonquin; Douglas Ceckowski, Gurnee; David Morrow, Chicago, all of IL (US)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/037,356

(22) Filed: Mar. 10, 1998

(51) Int. Cl.[7] .................................................. G06F 17/30
(52) U.S. Cl. ................................... 707/205; 422/67
(58) Field of Search .................... 707/200, 205; 700/266; 345/326; 356/39; 422/67

(56) References Cited

U.S. PATENT DOCUMENTS

| | | | |
|---|---|---|---|
| 4,827,430 | 5/1989 | Aid et al. | 700/285 |
| 5,496,265 | 3/1996 | Langley et al. | 604/6.01 |
| 5,581,687 | * 12/1996 | Lyle et al. | 345/326 |
| 5,611,997 | 3/1997 | Langley et al. | 422/73 |
| 5,629,871 | 5/1997 | Love et al. | 702/34 |
| 5,653,887 | 8/1997 | Wahl et al. | 210/745 |
| 5,658,240 | 8/1997 | Urdahl et al. | 604/601 |
| 5,681,273 | 10/1997 | Brown | 604/6.07 |
| 5,697,376 | 12/1997 | Nomura et al. | |
| 5,711,302 | 1/1998 | Lampropoulos et al. | |
| 5,712,798 | 1/1998 | Langley et al. | 700/266 |
| 5,735,286 | * 4/1998 | Notton et al. | 128/700 |
| 5,769,811 | * 6/1998 | Stacey et al. | 604/4 |
| 5,812,397 | 9/1998 | Pech et al. | 700/81 |

FOREIGN PATENT DOCUMENTS

| | | |
|---|---|---|
| WO96/40322 | 6/1996 | (WO) . |
| WO 96/40322 | 12/1996 | (WO) . |

OTHER PUBLICATIONS

Hartman, John H. et al. "Zebra: A Striped Network File System".

* cited by examiner

*Primary Examiner*—Wayne Amsbury
(74) *Attorney, Agent, or Firm*—Daniel D. Ryan; Bradford R. L. Price

(57) ABSTRACT

A device has processing hardware to carry out a blood processing procedure. A processing control manager resides on the device to monitor status conditions over time during the blood processing procedure. A data interface also resides on the device. The data interface includes a flash memory data storage medium formatted to allocate discrete block file spaces to receive data. Chronologic data or time-specific data are created based upon sensed conditions by a data generator task, which also resides on the device. A file manager task appends chronologic data to an allocated file space to create a chronologic block file, which, when read, provides a time-ordered account of processing activities or hardware conditions. The file manager also operates to block-write time-specific data to another allocated file space, which, when read, creates a snap-shot of processing conditions at a given point in time. The data file structure created on the flash memory medium withstands corruption of data due to power failure.

44 Claims, 19 Drawing Sheets

FIG. 14
PROCEDURE REPORT

Donation ID Number:
Instrument Number:

DONOR DATA

Donor ID Number:
Donor Sex:
Donation ID Number:
Selected Procedure:

ENTERED PROCEDURE VALUES

ACD Ratio:
Platelet Pre-Count:
Yield:
Whole Blood to Process:
Plasma Product Volume:
Citrate Infusion Rate:
Mean Platlet Volume:
Weight:
Hematocrit:
Storage Plasma Volume:

DISPOSABLE DATA

Kit Code:
Kit Lot Number:
Kit Expiration Date:

PROCEDURE RESULTS

ACD Used:
Saline Used:
ACD in Plama Product:
ACD in Storage Plasma:
Collection Time:
Whole Blood Processed:
Total Whole Blood Drawn:
Plasma Product Volume:
Storage Plasma Volume:
Total Warning Alarms:

FIG. 15

EVENT REPORT

DONATION ID NUMBER  01/26/1998
INSTRUMENT NUMBER  16:54 hrs

PROCEDURE EVENTS

- 16:54 hrs: Procedure Start
- 16:55 hrs: Mode: Install Kit
- 16:55 hrs: Mode: Prime
- 16:55 hrs: Empty ACD @ 0 ml WB Processed
- 16:56 hrs: Resume Procedure @ 16:56:04 hrs
- 16:56 hrs: Mode: Air Detector Test
- 16:56 hrs: Mode: Enter Parameters
- 16:56 hrs: WB to Process (ml): 0 →300 @ 0 ml WB Processed
- 16:56 hrs: WB to Process (ml): 300 →3000 @ 0 ml WB Processed
- 16:56 hrs: Weight (kg): 0 →170 @ 0 ml WB Processed
- 16:57 hrs: Citrate Infusion Rate mg/kg/min: 1.250 →1.500 @ 0 ml WB Processed
- 16:57 hrs: Mode: Procedure Setup
- 16:57 hrs: Start Needle Prime @ 16:57:07 hrs
- 16:57 hrs: Stop Needle Prime @ 16:57:13 hrs
- 16:57 hrs: Kit Lot Number: H95G18011
- 16:57 hrs: Kit Expiration Date 19970131
- 16:57 hrs: Kit Lot Number: H95G18011
- 16:57 hrs: Kit Lot Number: H95G18011
- 16:58 hrs: Kit Lot Number: H95G18011
- 16:58 hrs: Kit Expiration Date: 19970131
- 16:58 hrs: Donor Sex: Male
- 16:58 hrs: NaCl Lot Number: (NaCl Lot Number)
- 16:58 hrs: NaCl Prod Code: (NaCl Product Code)
- 17:00 hrs: Procedure Paused @ 17:00:18 hrs
- 17:00 hrs: Mode: Procedure Wrap-Up
- 17:00 hrs: Mode: Product Transfer
- 17:01 hrs: Mode: Remove Kit
- 17:01 hrs: Procedure End

SYSTEMS AND METHODS FOR STORING, RETRIEVING, AND MANIPULATING DATA IN MEDICAL PROCESSING DEVICES

FIELD OF THE INVENTION

The invention relates to systems and methods for recording data during the course of fluid processing procedures, such as those carried out by blood processing systems and the like.

BACKGROUND OF THE INVENTION

Today people routinely separate whole blood by centrifugation into its various therapeutic components, such as red blood cells, platelets, and plasma.

These and other medical processing devices are often controlled using microprocessors with resident program software. The microprocessors also usually include some type of interface through which the operator views and comprehends information regarding the operation of the fluid processing systems.

These and other medical processing devices also often require the ability to record key control and processing parameters during the course of a procedure, as well as to keep track of operator intervention during the procedure. These data recording functions are useful, as they support, e.g., GMP requirements, instrument trouble shooting and problem diagnosis, and instrument performance evaluation. Still, while important, data recording functions should not compete or interfere with the overall processing tasks and objectives of the procedure.

As the operational and performance demands upon such fluid processing systems become more complex and sophisticated, the need exists for integrating, automating, and fortifying data recording functions.

SUMMARY OF THE INVENTION

The invention provides systems and methods, which fully integrate data recording functions with processing functions. Thus, the same instrument that carries out the processing tasks also performs the data recording functions, without the need for add-on, external data recording systems.

The invention also provides systems and methods, which fully automate necessary data recording functions, so that they can be accomplished "in the background," without significant operator intervention or control.

The invention also provides robust systems and methods, which carry out data recording functions that withstand real world abuse, such as power failure or corruption of stored data. This "crash-proof" aspect is particularly significant in an embedded software systems environment, where an instrument may be powered off at any time.

One aspect of the invention provides systems and methods for processing data during a blood processing procedure. The systems and methods monitor status conditions over time during the blood processing procedure and generate data based upon monitored status conditions. The systems and methods write the data to a flash memory storage medium. In a preferred embodiment, the systems and methods retrieve and manipulate the data written to the flash memory storage medium.

The use of flash memory provides reliability and compact size, so that robust data storage, retrieval, and processing functions can be carried out on-board a blood processing device, without need for external computing devices and without concern about the durability and reliability of the data storage functions.

According to another aspect of the invention, blood processing systems and methods employ a device that has processing hardware to carry out a blood processing procedure. A processing control manager resides on the device to monitor status conditions over time during the blood processing procedure. A data interface also resides on the device. The data interface includes a data storage medium formatted to allocate discrete block file spaces to receive data.

In a preferred embodiment, chronologic data or time-specific data can be created, based upon sensed conditions by a file generator task, which resides on the device. A file manager task operates to append chronologic data in an allocated file space to create a chronologic block file. When read, the chronologic block file provides a time-ordered account of processing activities or hardware conditions. The file management element also operates to block-write time-specific data to another allocated file space. When read, each time-specific data file provides a snap-shot of processing conditions at a given point in time. The data file structure created withstands corruption of data due to power failure.

The features and advantages of the invention will become apparent from the following description, the drawings, and the claims.

BRIEF DESCRIPTION OF THE DRAWINGS

FIG. 14 is a representative Procedure Report that the data interface shown in FIG. 7 can generate;

FIG. 15 is a representative Event Report that the data interface shown in FIG. 7 can generate;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DESCRIPTION OF THE PREFERRED EMBODIMENTS

Figure 1:
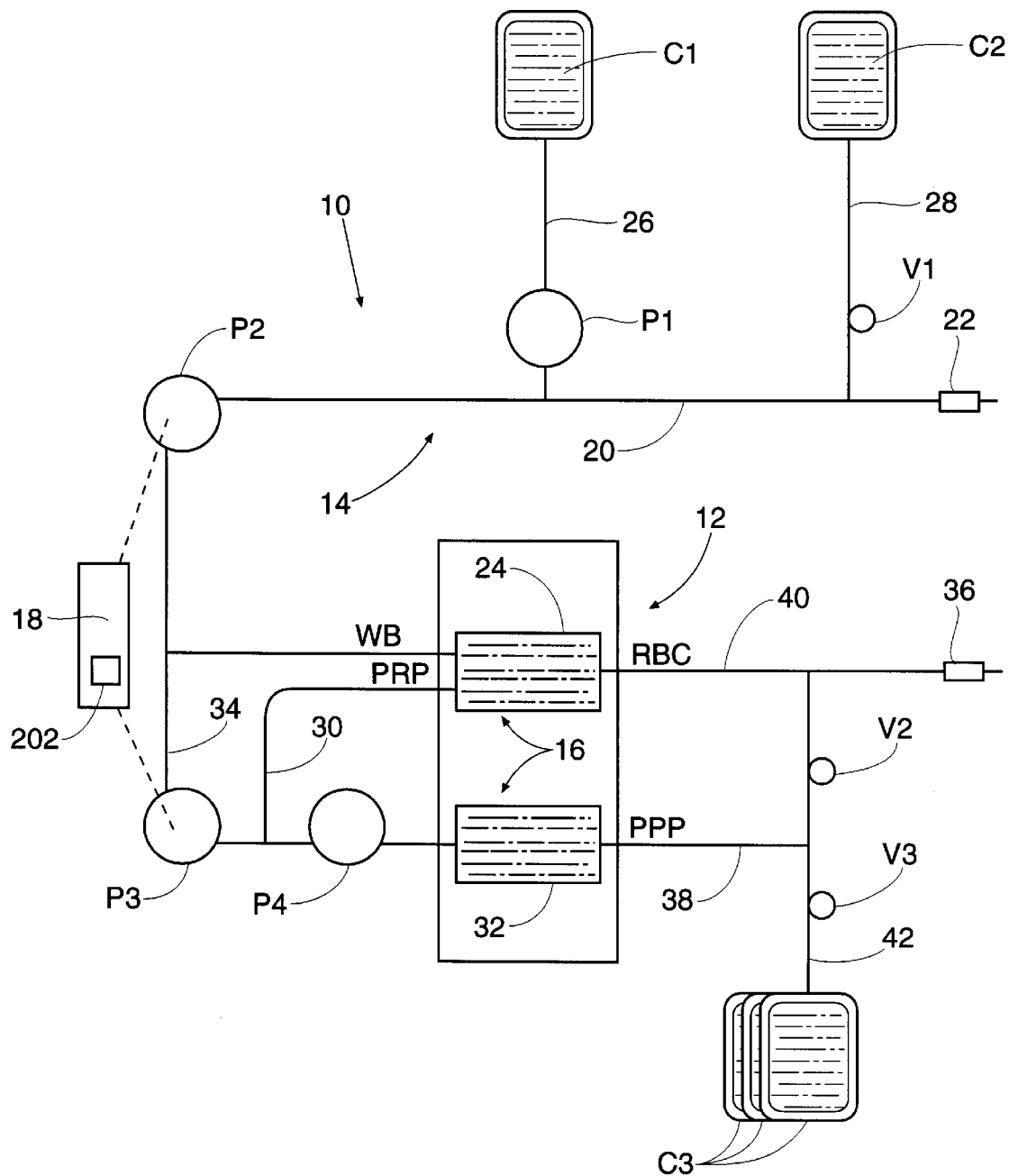
FIG. 1 is a diagrammatic view of a dual needle platelet collection system that includes a controller that embodies the features of the invention.

FIG. 1 shows in diagrammatic form a fluid processing system 10. The system 10 can be used for processing various fluids. The system 10 is particularly well suited for processing fluids for medical purposes, like whole blood and other suspensions of biological cellular materials. Accordingly, the illustrated embodiment shows the system 10 used for this purpose.

I. The Separation System

The system 10 includes an arrangement of durable hardware elements. The hardware elements will vary according to the nature and type of processing system. In the context of processing whole blood, the hardware elements will include a centrifuge 12, in which whole blood (WB) is separated into its various therapeutic components, like platelets, plasma, and red blood cells (RBC). The hardware elements will also include various pumps, which are typically peristaltic (designated P1 to P4); and various in line clamps and valves (designated V1 to V3). Of course, other types of hardware elements will typically be present, which FIG. 1 does not show, like solenoids, pressure monitors, and the like.

The system 10 typically also includes some form of a disposable fluid processing assembly 14 used in association with the hardware elements.

In the illustrated blood processing system 10, the assembly 14 includes a two stage processing chamber 16. In use, the centrifuge 12 rotates the processing chamber 16 to centrifugally separate blood components.

The construction of the two stage processing chamber 16 can vary. For example, it can take the form of double bags, like the processing chambers shown in Cullis et al. U.S. Pat. No. 4,146,172. Alternatively, the processing chamber 16 can take the form of an elongated two stage integral bag, like that shown in Brown U.S. Pat. No. 5,370,802.

In the illustrated blood processing system 10, the processing assembly 14 also includes an array of flexible tubing that forms a fluid circuit. The fluid circuit conveys liquids to and from the processing chamber 16. The pumps P1–P4 and the valves V1–V3 engage the tubing to govern the fluid flow in prescribed ways. The fluid circuit further includes a number of containers (designated C1 to C3) to dispense and receive liquids during processing.

A controller 18 governs the operation of the various hardware elements to carry out one or more processing tasks using the assembly 14. The invention specifically concerns important attributes of the controller 18.

The system 10 can be configured to accomplish diverse types of blood separation processes. FIG. 1 shows the system 10 configured to carry out an automated two needle platelet collection procedure.

In a collection mode, a first tubing branch 20 and the whole blood inlet pump P2 direct WB from a draw needle 22 into the first stage 24 of the processing chamber 16. Meanwhile, an auxiliary tubing branch 26 meters anticoagulant from the container C1 to the WB flow through the anticoagulant pump P1.

The container C2 holds saline solution. Another auxiliary tubing branch 28 conveys the saline into the first tubing branch 20, via the in line valve V1, for use in priming and purging air from the system 10 before processing begins. Saline solution is also introduced again after processing ends to flush residual components from the assembly 14 for return to the donor.

Anticoagulated WB enters and fills the first stage 24 of the processing chamber 24. There, centrifugal forces generated during rotation of the centrifuge 12 separate WB into red blood cells (RBC) and platelet-rich plasma (PRP).

The PRP pump P4 operates to draw PRP from the first stage 24 of the processing chamber 16 into a second tubing branch 30 for transport to the second stage 32 of the processing chamber 16. There, the PRP is separated into platelet concentrate (PC) and platelet-poor plasma (PPP).

The system 10 includes a recirculation tubing branch 34 and an associated recirculation pump P3. The processing controller 18 operates the pump P3 to divert a portion of the PRP exiting the first stage 24 of the processing chamber 16 for remixing with the WB entering the first stage 24 of the processing chamber 16.

As WB is drawn into the first chamber stage 24 for separation, the illustrated two needle system simultaneously returns RBC from the first chamber stage 24, along with a portion of the PPP from the second chamber stage 32, to the donor through a return needle 36 through tubing branches 38 and 40 and in line valve V2.

The system 10 also collects PC in some of the containers C3 through tubing branches 38 and 42 and in line valve V3 for storage and therapeutic use. The system 10 can also collect PPP in some of the containers C3 through the same fluid path.

II. The System Controller

The controller 18 carries out the overall process control and monitoring functions for the system 10 as just described.

Figure 2:
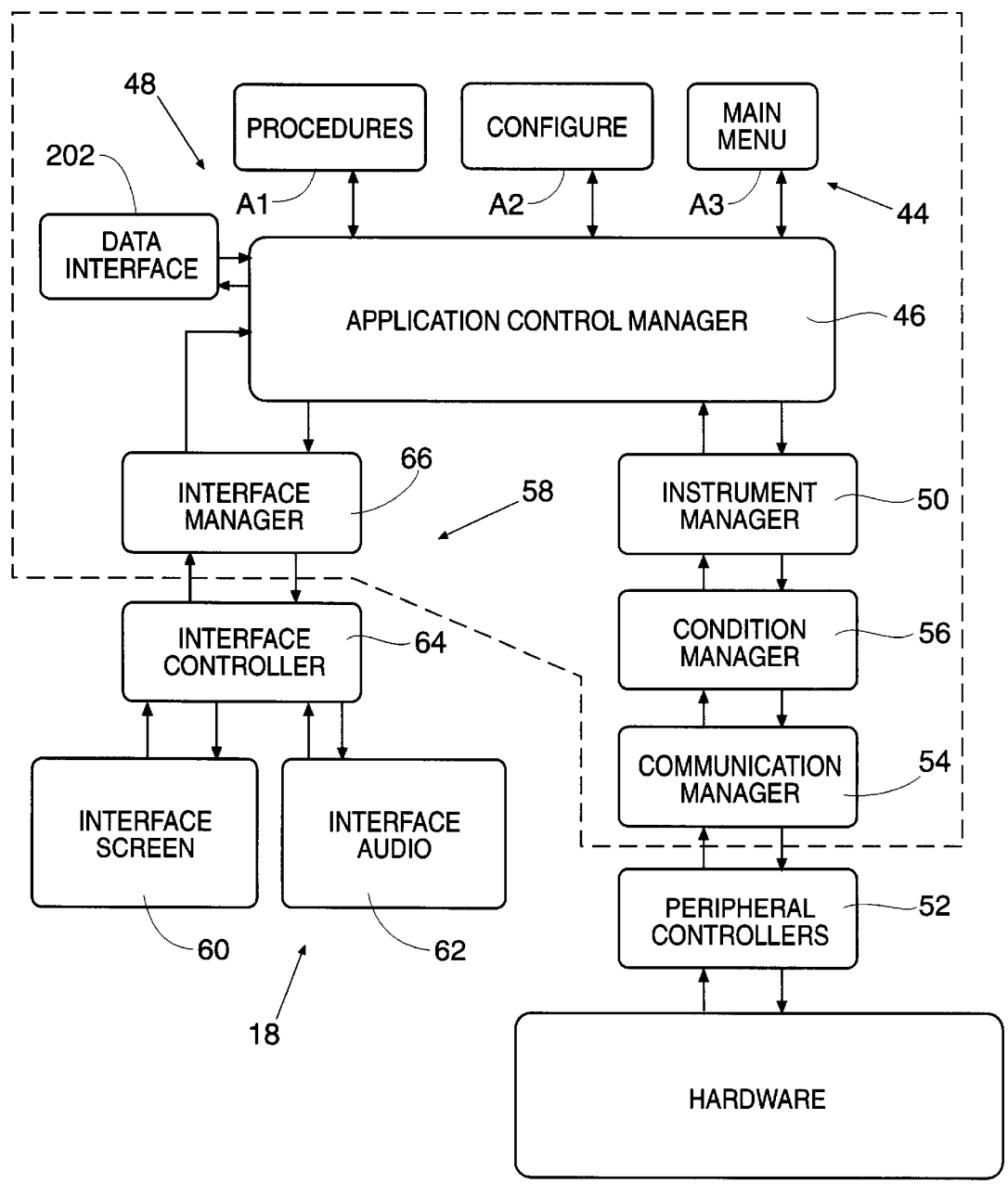
FIG. 2 is a diagrammatic flow chart view of the controller and the associated instrument manager and graphical user interface.

In the illustrated and preferred embodiment (see FIG. 2), the controller comprises a main processing unit (MPU) 44. In the preferred embodiment, the MPU 44 comprises a type 68030 microprocessor made by Motorola Corporation, although other types of conventional microprocessors can be used.

In the preferred embodiment, the MPU 44 employs conventional real time multi-tasking to allocate MPU cycles to processing tasks. A periodic timer interrupt (for example, every 5 milliseconds) preempts the executing task and schedules another that is in a ready state for execution. If a reschedule is requested, the highest priority task in the ready state is scheduled. Otherwise, the next task on the list in the ready state is schedule.

A. Functional Hardware Control

The MPU 44 includes an application control manager 46. The application control manager 46 administers the activation of a library 48 of control applications (designated A1 to A3). Each control application A1–A3 prescribes procedures for carrying out given functional tasks using the system hardware (e.g., the centrifuge 12, the pumps P1–P4, and the valves V1–V3) in a predetermined way. In the illustrated and preferred embodiment, the applications A1–A3 reside as process software in EPROM's in the MPU 44.

The number of applications A1–A3 can vary. In the illustrated and preferred embodiment, the library 48 includes at least one clinical procedure application A1. The procedure application A1 contains the steps to carry out one prescribed clinical processing procedure. For the sake of example in the illustrated embodiment, the library 48 includes a procedure application A1 for carrying out the dual needle platelet collection process, as already generally described in connection with FIG. 1. Of course, additional procedure applications can be, and typically will be, included. For example, the library 48 can include a procedure application for carrying out a conventional single needle platelet collection process (A1').

In the illustrated and preferred embodiment, the library 48 also includes at least one additional, non-procedure application. The non-clinical procedural application contains the procedures to carry out a system configuration or support utility. For the sake of example in the illustrated embodiment, the library 48 includes a configuration application A2, which contains the procedures for allowing the operator to configure the default operating parameters of the system 10. The library 48 also includes a main menu application A3, which coordinates the selection of the various applications A1–A3 by the operator, as will also be described in greater detail later.

Of course, additional non-clinical procedure applications can be, and typically will be, included. For example, the library 48 can include a diagnosis application, which contains the procedures aiding service personnel in diagnosing and troubleshooting the functional integrity of the system, and a system restart application, which performs a full restart of the system, should the system become unable to manage or recover from an error condition.

An instrument manager 50 also resides as process software in EPROM's in the MPU 44. The instrument manager 50 communicates with the application control manager 46. The instrument manager 50 also communicates with low level peripheral controllers 52 for the pumps, solenoids, valves, and other functional hardware of the system.

Figure 3:
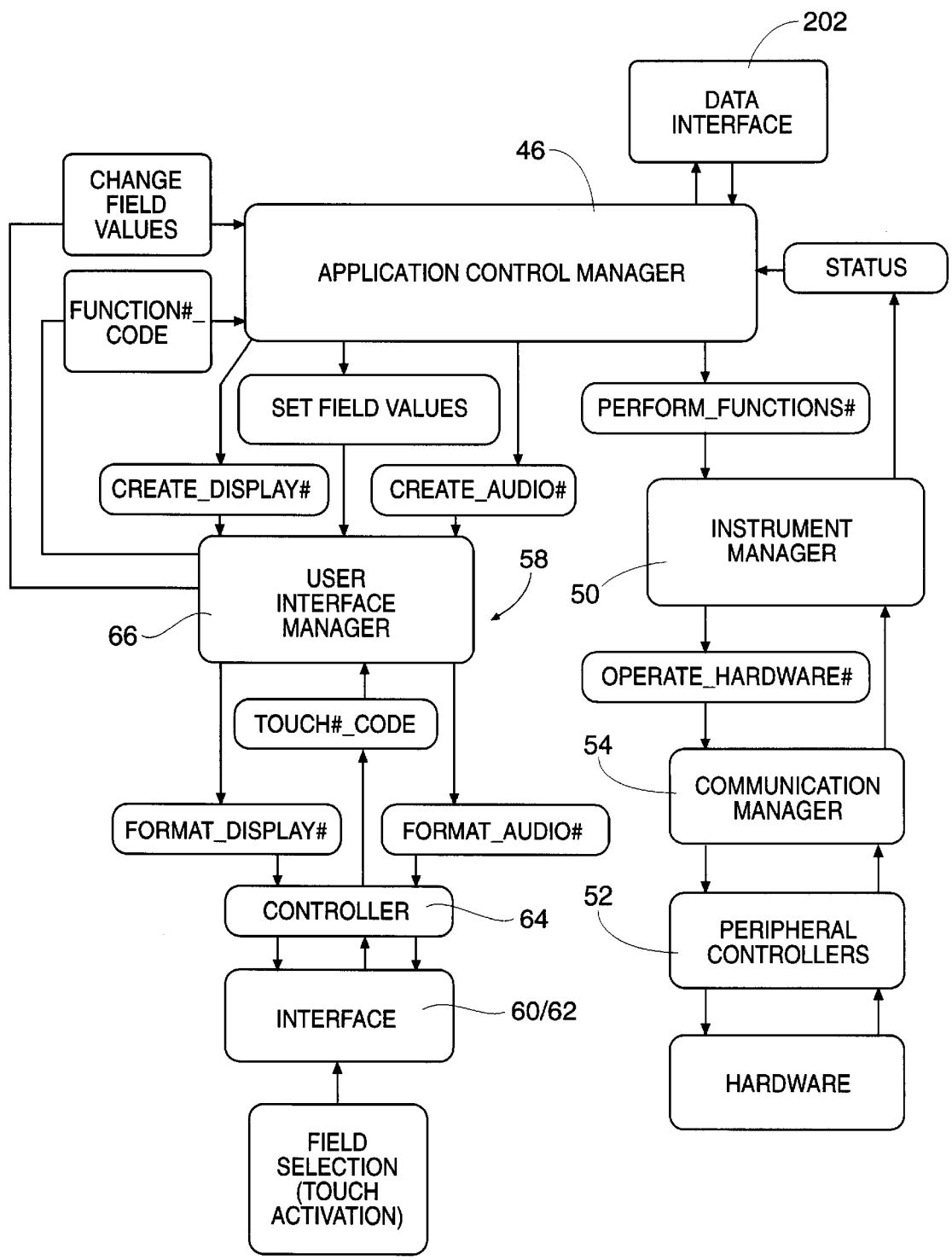
FIG. 3 is another diagrammatic view of the controller and the associated instrument manager and graphical user interface shown in FIG. 2, and further showing the command and status flow hierarchy.

As FIG. 3 shows, the application control manager 46 sends specified Perform_Function# commands in abstract form to the instrument manager 50, as called up by the activated application A1–A3. In response to these abstract commands, the instrument manager 50 identifies the peripheral controller or controllers 52 for performing the function and compiles hardware-specific Operate_Hardware# commands into the command tables for the particular peripheral controllers 52. The peripheral controllers 52 communicate directly with the hardware to implement the hardware-specific commands generated by the instrument manager 50, causing the hardware to operate in a specified way to carry out the abstract Perform_Function# commands. A communication manager 54 manages low-level protocol and communications between the instrument manager 50 and the peripheral controllers 52.

As FIG. 3 also shows, the instrument manager 50 also conveys back to the application control manager 46 status data about the operational and functional conditions of the processing procedure. The status data is expressed in terms of, for example, fluid flow rates, sensed pressures, and fluid volumes measured.

The application control manager 46 processes and uses the status data in various ways. In one way, the application control manager 46 transmits selected status data for display to the operator, as will be described later. In another way, the application control manager 46 monitors operational and functional conditions using the status data to detect abnormal system conditions requiring operator intervention or system shutdown.

In the preferred embodiment (see FIG. 2), the MPU 44 also includes a condition manager 56 that resides in the data flow path between the instrument manager 50 and the communications manager 54. The condition manager 56 also monitors status data and other operational states of the hardware to detect abnormal conditions that are either not detected or are left uncorrected by the application control manager 46. Upon detecting such abnormal conditions, the condition manager 56 provides fail-safe support by suspending system operation.

The described control hierarchy creates an abstract, "virtual" interface between the applications resident in the application control manager 46 and the hardware elements of the system 10. The high level process software resident in the application control manager 46 communicates with lower level implementing process software in the instrument manager 50, instead of communicating directly with hardware elements. In this way, the intermediate instrument manager 50 isolates or "hides" all hardware-specific commands from the application control manager 46. The applications pass abstract Perform_Function# commands to the instrument manager 50, and the instrument manager 50 converts these abstract commands into the specific Operate_Hardware# commands unique to the particular hardware elements, all without further participation by the procedure applications A1–A3 themselves. The data flow between the instrument manager 50 and the hardware elements of the system 10 is invisible to the activated application A1–A3.

The creation of the virtual interface between high level process software and the hardware elements provides considerable flexibility in adding or modifying the process software of the high level applications A1–A3 for controlling hardware functions. New or modified process software for the applications need only to include specified hardware-non-specific abstract Perform_Function# commands to gain immediate linkage to the virtual hardware interface. Likewise, addition or modification of specific hardware requires only changes to the low level process software of the instrument manager 50. Because of the virtual interface, hardware changes require minimal changes to the high level software in the application control manager 46.

As described above, the instrument manager 50 forms a part of the same MPU in which the application control manager 46 resides. Alternatively, because of the virtual nature of the interface, the instrument manager 50 can reside on a separate processing unit.

B. User Interface Control

In the illustrated embodiment, the MPU 44 also includes an interactive user interface 58. The interface 58 allows the operator to view and comprehend information regarding the operation of the system 10. The interface 58 also allows the operator to select applications residing in the application control manager 46, as well as to change certain functions and performance criteria of the system 10.

The interface 58 includes an interface screen 60 and, preferably, an audio device 62. The interface screen 60 displays information for viewing by the operator in alphanumeric format and as graphical images. The audio device 62 provides audible prompts either to gain the operator's attention or to acknowledge operator actions.

In the illustrated and preferred embodiment, the interface screen 60 also serves as an input device. It receives input from the operator by conventional touch activation, as will be described later. Alternatively or in combination with touch activation, a mouse or keyboard could be used as input devices.

An interface controller 64 communicates with the interface screen 60 and audio device 62. The interface controller 64, in turn, communicates with an interface manager 66, which in turn communicates with the application control manager 46. The interface controller 64 and the interface manager 66 reside as process software in EPROM's in the MPU 44.

In use, the application control manager 46 sends to the interface manager 66 specified field values reflecting selected status data received from the instrument manager 50. The application control manager 46 also sends to the interface manager 66 prescribed abstract Create_Display# and Create_Audio# commands called for by the activated application.

The interface manager 66 processes these field values and the abstract Create_Display# commands to generate specific Format_Display# commands. The Format_Display# commands control the particular format, attributes, and protocols necessary to create, refresh, and close the visual display on the interface screen 60.

Likewise, the interface manager 66 processes the abstract Create_Audio# commands to generate specific Format_Audio# commands. The Format_Audio# commands dictate the format and attributes of the audio output called for by the activated application.

The interface manager 66 conveys the processed Format_Display# and _Audio# commands to the interface controller 64. The interface controller 64 provides low level control functions that draw boxes and lines, forms text or graphical characters, and provides the formatting ant attributes of the display on the interface screen 60. The interface controller 64 also provides low level control functions that drive the audio device 62 based upon Format_Audio# commands received from the interface manager 66.

The interface controller 64 also accepts Field#_Select commands generated by touch activation of the interface screen 60, as will be described in greater detail later. The interface controller 64 passes this touch activated input to the interface manager 66 in the form of Touch#_Codes. The interface manager 66 processes the Touch#_Codes to the application control manager 46, either as function codes or as changed field values. The application control manager 46 implements the function codes or changed field values and passes them to the instrument manager 50.

This control hierarchy also creates an abstract, "virtual" interface between the functional processors of the controller 18 and the interface 58. The high process software of the interface manager 66 isolates and "hides" all formatting and protocol issues used in creating the interface 58 from the applications used to control hardware functions of the system 10. The process software of the applications A1–A3, through the application control manager 46, pass abstract field values and Create_Display# and Create_Audio# commands to the interface manager 66. The process software of the interface manager 66 converts these abstract commands into the specific commands that control the textual and graphic formats and audio formats of the operator interface 58, without further participation by the procedure applications A1–A3 themselves. The data flow between the interface manager 66 and the interface controller 64 is invisible to the data flow between the application control manager 46 and the instrument manager 50.

This control hierarchy lends further flexibility in adding or modifying applications for controlling hardware functions. New or modified applications need only to include textual field value outputs and the prescribed Create_Display# or Create_Audio# commands to gain immediate linkage to the operator interface.

(I) Interface Screen Format

In the illustrated and preferred embodiment (see FIG. 4), the Format_Display# commands of the interface manager 66 formats information for display on the interface screen 60 in two distinct viewing regions, called the status region 68 and the working region 70. Preferably, the two viewing regions 68 and 70 are fixed in relative position and unchanging in size on the interface screen 60. This provides continuity and consistency to the appearance of the interface 58, even as the functional hardware of the system cycle through different processing modes. The uniformity and consistency of the dual viewing regions 68 and 70 of the interface 58 reduce operator confusion and the likelihood of error.

The status region 68 and the working region 70 are each dedicated to different types and levels of information. Nevertheless, the two regions 68 and 70 are always displayed simultaneously to provide the operator views of both high level "big picture" information and low level "detailed" information.

The working region 70 provides the means for the operator to select and activate any one of the system-resident applications A1–A3. The working region 70 displays all specific procedure-dependent information then called for by the Create_Display# commands generated by the activated application A1–A3. The considerable detail of information displayed in the working region 70 allows the operator to monitor and change the ongoing process in real time.

On the other hand, the status region 68 continuously shows prescribed procedure-dependent information of a more general and "overview" nature, about which a operator routinely needs continuous knowledge and immediate access. The status region 68 continuously displays this general information to keep the operator appraised of the overall status of the ongoing process, even when the operator is using the working region 70 to monitor and change more detailed aspects of the processes. In the illustrated and preferred embodiment, the status region 68 also provides means for the operator to respond to alarms or malfunctions.

The two viewing regions 68 and 70 allow the operator to use the interface 58 quickly to find and select among detailed procedures, functions, and options during system operation, or to perform offline functions, without losing touch with the overall status of the ongoing procedure. The two viewing regions 68 and 70 permit the operator to navigate what is in reality a multiple-level menu structure to attend to details on one menu level, without necessarily moving in steps up and down the menu structure and without losing the ability to, on command, immediately jump between higher and lower menu levels.

In the illustrated embodiment, the viewing regions 68 and 70 are vertically separated by a graphical line or line of characters 72, with the status region 68 occupying the upper one-third of the screen 60 and the working region 70 occupying the lower two-thirds of the screen 60. It should be appreciated, however, that the viewing regions 68 and 70 could be separated horizontally in a side by side relationship, and occupy differing proportions of the screen 60.

The status region 68 and the working region 70 display information in fields. The Format_Display# for the particular display that the interface manager 66 generates is composed of a list of such fields specifying, for each field, its location, size, and type in the region and the format of information it contains.

As will be discussed in greater detail later, the fields can formatted as individual touch selectable buttons. The fields can also be formatted as an array of touch selectable button fields, which present a field of choices to the operator.

The fields can also be formatted as blocks comprising alpha or numeric data strings, or textual data comprising multiple lines of line-wrapped, scrollable text, or graphic images. The fields can also be formatted to be bar graph fields, which display numeric format in graphical form.

The interface manager 66 includes constant (ROM-based) structures in look-up table form that store data describing the layout and formatting of all display attributes, including regions, field type, and field location within the regions. The interface manager 66 stores dynamic (RAM-based) structures that describe the present state of the interface display. Upon receiving a given Create_Display# command from the activated application, the interface manager 66 examines the ROM-based table structures and the RAM-based status structures to create or update the RAM-based status structures, as called for by the activated application. The interface manager 66 includes a time-triggered task routine that performs all operations required to periodically update screen 60 and audio outputs. The interface manager 66 sends this processed information to the interface controller 64 for implementation.

The interface manager 66 also holds a Function#_Code associated with each touch selectable button field identified by the Touch#_Code received from the interface controller 64. The Function#_Codes are arranged in constant (ROM-based) look-up table form according to region and field location within the region, as identified by the Touch#_Code. The interface controller 64 registers the region and field location when a given button is touched, passing this information in the form of a Touch#_Code to the interface manager 66. The interface manager 66 includes a process button utility that awaits and asynchronously processes this information by examining the ROM-based table structure and sending the appropriate Function#_Code to the application control manager 46 for implementation.

The information and format selected for display in the status region 68 and the working region 70 can vary.

a. The Status Region

In the illustrated embodiment (see FIG. 4), the status region 68 includes a MAJOR MODE field 74, which contains the description of the clinical procedure activated; a MINOR MODE field 76, which contains a one or two word description of the procedure status; and a WB PROCESSED field 78, which contains the amount of blood drawn from the donor through the draw pump P2 during processing, expressed numerically in units of ml.

In the illustrated embodiment (FIG. 4), the status region 68 also includes an array of touch selectable button fields, labeled, e.g., HELP 80, MAIN MENU 82, PROCEDURE DISPLAY 84, and PAUSE/END 86. When touched, each cause the interface manager 66 to transmit a prescribed function code for implementation by the application control manager 46, without altering the display of information in the blocks fields 74/76/78 on the status region 68.

The status region 68 also includes context-dependent NOTE/WARNING PROMPT button field 88 that occupies a fixed location on the right side, top position, of the status region 68 when an alarm or warning is active. The NOTE/WARNING PROMPT button field 88 is not displayed when an alarm or warning is not active. A MUTE button field 90 also occupies a fixed location on the left side, top position, of the status region 68 when an alarm is active. A WARNING/ALARM block field also occupies a fixed location on the center, bottom position, of the status region when an alarm is active. b. The working Region In the illustrated and preferred embodiment, the working region 70 shows by default the Main Menu display called for by the main menu application A3. The Main Menu display includes an array of touch selectable button fields 94 and 96.

Figure 5:
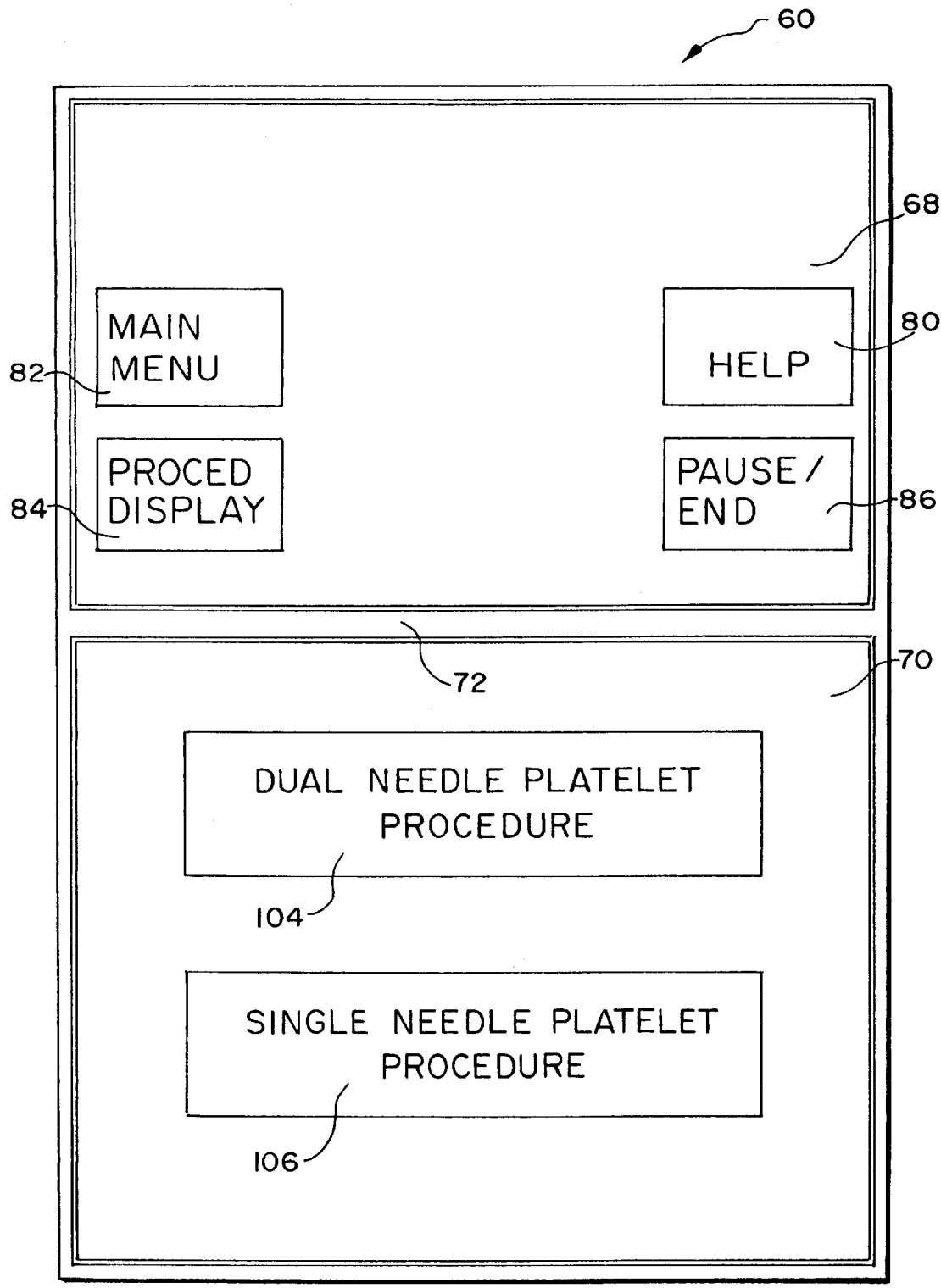
FIG. 5 a view of the dual region interface screen, showing the Select Procedures Submenu in the working region of the interface screen.

When touched, the CHOOSE PROCEDURE button field 94 calls up a function that displays a Procedure Submenu in the working region 70 (see FIG. 5). The Procedure Submenu lists in an array of touch selectable button fields 104 and 106 all clinical procedure applications administered by the application control manager 46, which in the illustrated implementation is the Dual Needle Procedure Application A1 and the Single Needle Procedure Application A1'. When touched, a procedure application button field calls up a function that directs the application control manager 46 to activate the associated application. The activated application generates its own designated Create_Display# commands, which the interface manager 66 implements to change the display in the working region 70.

When touched, the SPECIAL FEATURES button field 96 calls up a function that displays a Special Features Submenu in the working region 70 (see FIG. 6). The Features Submenu lists in an array of touch selectable button fields 200 designated non-clinical procedure specific applications administered by the application control manager 46. When a given special procedures application button is touched, that application is activated and the display in the working region 70 changes in response to the Create_Display# commands of the activated application. Further details of certain buttons in the fields 200 will be provided later.

Further details of the controller 18 and the graphical user interface manager 66 as described can be found in U.S. Pat. No. 5,581,687, which is incorporated herein by reference.

C. The Data Interface

In the illustrated and preferred embodiment (see FIG. 7), the controller 18 also includes a data interface 202. The data interface 202 forms self-contained, integrated part of the software and hardware architecture of the controller 18. The data interface 202 automates the collection, retention, and manipulation of key control and processing parameters and operator steps during a given processing application. The data interface 202 retains the information in a data structure in a mass data storage device 204, which also forms an integral part of the controller 18. The data structure of the storage device 204 permits information to be stored, retrieved, and manipulated in a secure fashion, which is resistant to corruption due to unexpected loss of power. The data structure of the storage device 204 also permits stored information to be retrieved and formatted into printed reports.

While not essential to its operation, the data interface 202 can also, if desired, be linked to one or more external computers 206 and 206'. The data interface 202 can download stored information to the computers 206 206' in either a structured or an arbitrary order, as will be described in greater detail later.

The data interface 202 can be implemented in various ways. In the preferred embodiment, the mass storage device 204 comprises a flash memory card, e.g., one conforming to the PCMCIA Type II, PC Card ATA standard hardware interface. Conventionally, the flash memory storage device 204 can support storage ranges from 2 to 85 megabytes. In a typical implementation, the flash memory storage device 204 can hold about 8 megabytes of data.

The flash memory storage device 204 lends itself to use with the integrated data interface 202, compared to conventional hard drive storage mediums. The flash memory device 204 provides ease of formatting and fast data access time. The flash memory device 204 presents a small compact size, which does not compete for space with blood processing hardware. The flash memory device 204 has no mechanical components, and is therefore extremely reliable and is not prone to failure caused by repeated use. The flash memory device 204 also is durable, being resistant to vibration and other forces that a centrifugal blood processing device routinely generates during a blood processing procedure. The flash memory device 204 also is easy to service and replace on site.

The data interface 202 also includes additional hardware input/output devices 208, 210, 212, and 348, which can take the form of, e.g., conventional serial RS-232C port links. Other input/output devices, such as conventional parallel port links and one or more or Ethernet™ communication links, can be used.

In the illustrated embodiment (see FIG. 7), one port link 208 communicates with an external a bar code scanner 214. A second port 210 communicates with one external computer 206, previously described. A third port link 212 communicates with an external printer 216. A fourth port link 348 communicates with the other external computer 206'.

The data interface 202 also includes various process software modules 218 to 230 residing in EPROM's in the MPU 44. The process software modules 218 to 230 carry out prescribed data processing tasks.

The number and type of software modules 218 to 230 can vary. In the illustrated embodiment, one module 218 implements a COMMUNICATIONS MANAGER task. The COMMUNICATIONS MANAGER task module 218 handles lower level data transfers to and from the RS-232C port links 208, 210, 212, and 348. The COMMUNICATIONS MANAGER task module 218 prevents the MPU 44 from transferring data faster than it can be transmitted by the respective RS-232C port links 208, 210, 212, and 348.

Another module 220 implements a BAR CODE task. The BAR CODE task module 220 receives raw ASCII data input from the bar code scanner 214, received through the bar code scanner port link 208. The BAR CODE task module 220 parses the scanned data and assembles it into an input compatible with another module, called the PROCEDURE DRIVER TASK module 222, which will be described in greater detail later. The PROCEDURE DRIVER TASK module 222 also confirms that the scanned data has registered the scanned input, and, once confirmed, the BAR CODE task module 220 formats a feedback message output 232, as will be described later.

The data interface 202 also includes other core processing modules, which implement, respectively, a PROCEDURE DRIVER task, a FILE SYSTEM task, a REPORT task, a DATA EXCHANGE task, a DATA DUMP task, and a USER INTERFACE task. The details of these tasks will now be described.

(I) The Procedure Driver Task

The PROCEDURE DRIVER task module 222 receives information from the application control manager 46 and the BAR CODE task module 220. The PROCEDURE DRIVER task module 222 registers through the application control manager 46 designated key control and status information relating to the procedure then underway, as well as designated key control and status information relating to the pumps, solenoids, valves, optical detectors, and other functional hardware of the system. The PROCEDURE DRIVER task module 222 generates data containing this registered information, along with a date stamp to provide a time-based context. The data are structured byte streams, which are further processed by the FILE SYSTEM task module 224 for storage, retrieval, or manipulation.

The nature and type of the data that the PROCEDURE DRIVER task module 222 generates can vary.

a. Procedure Data (the P Data)

In the illustrated embodiment, the PROCEDURE DRIVER task module 222 registers all scanned bar code input, which can comprise, e.g., information identifying the donor, the processing instrument, and disposable components used for processing. The PROCEDURE DRIVER task module 222 also registers from the application control manager all key processing parameter and blood component yield values, as they are initialized and as they are updated during the course of the procedure.

The PROCEDURE DRIVER task module 222 also registers all processing mode changes as well as all warning alarms generated. In the illustrated embodiment, the PROCEDURE DRIVER task module 222 also registers designed special processing events, e.g., the start and stop of needle priming, as well as the pausing and resumption of a procedure.

Figure 7:
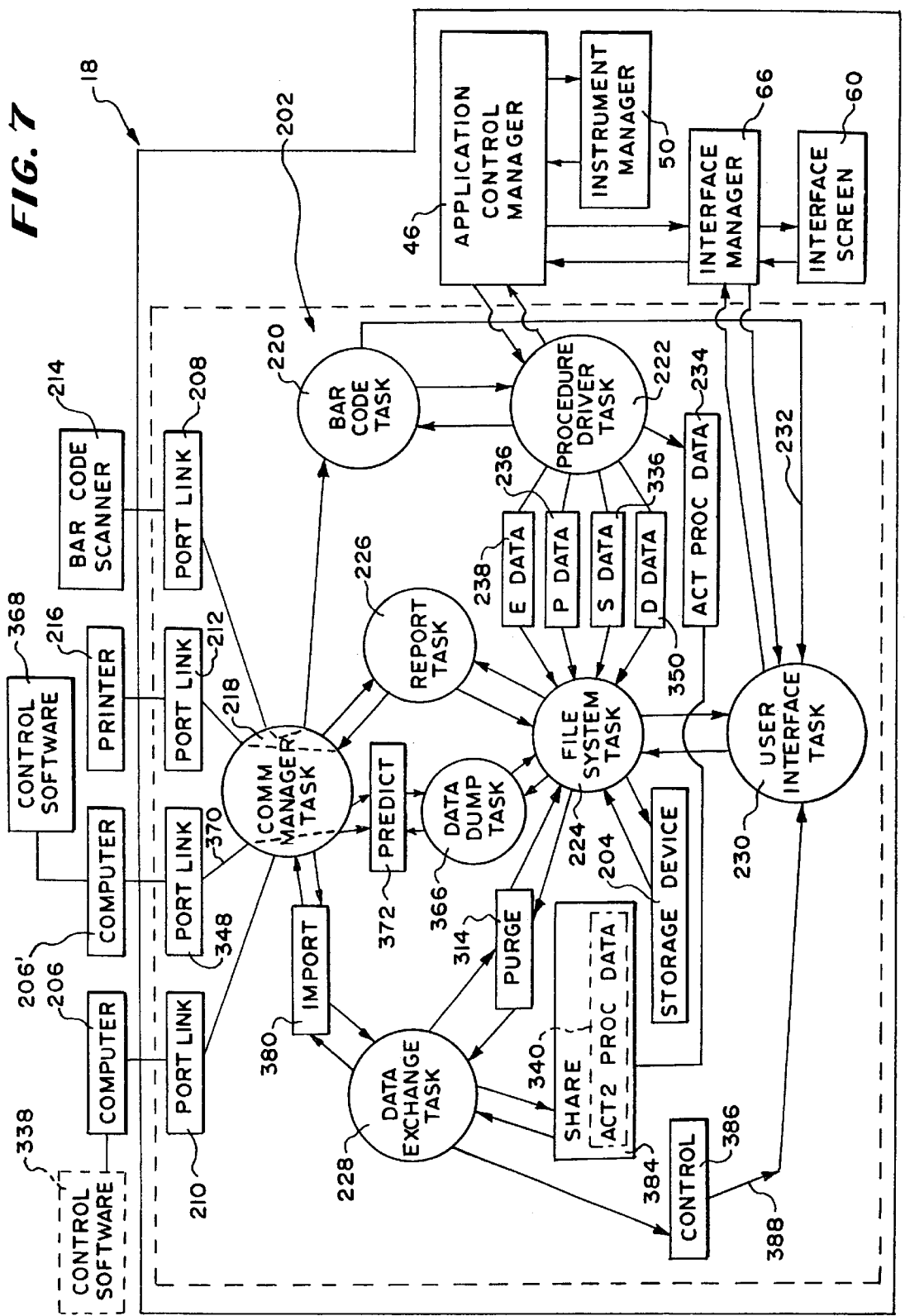
FIG. 7 is a diagrammatic flow chart view of the controller and the associated data interface.

The PROCEDURE DRIVER task module 222 establishes and maintains a random access data file, called Act_Proc_Data (designated 234 in FIG. 7). The contents of Act_Proc_Data file 234 comprise selected control and processing parameters. In the illustrated embodiment, the Act_Proc_Data file 234 is a fixed length file, which is formatted as a template to hold data in a prescribed order. Active procedure data is periodically written (e.g., every 15 seconds) to designated locations in the template of the Act_Proc Data file 234.

The current Act_Proc_Data file 234 therefore reflects the real time status of significant control and processing parameters and data for the procedure then underway. The parameters and data retained by the Act_Proc Data file 234 can include, e.g.,(I) donor identification information (e.g., an assigned donor I.D. number, donor sex and weight, an assigned blood donation I.D. number, and selected blood processing procedure);(ii) identification of the instrument and the disposable components used for processing (e.g., by assigned instrument number and disposable kit code, lot number, and expiration date); (iii) initial processing parameter values derived (e.g., anticoagulant ratio, platelet precounts, whole blood hematocrit, whole blood volume to be processed, volume of plasma to collect, platelet yield, mean platelet volume, storage volume of plasma for the platelets collected, volume of citrate returned to the donor, etc.); and (iv) then active procedure data (e.g., anticoagulant and saline used, anticoagulant and saline present in product and storage plasma, the collection time of the procedure, amount of WB processed, total WB drawn, total plasma storage and product plasma collected).

In the illustrated embodiment, at the end of the procedure (and, if desired, periodically during the procedure (e.g., every 15 seconds)), the PROCEDURE DRIVER task module 222 generates time stamped procedure data 236, which, in shorthand, are called "P Data" in FIG. 7. The procedure data 236 is a snap-shot of the information held in the thencurrent Act_Proc_Data file 234.

The procedure data 236 is formatted according to the template of the Act_Proc_Data file 234. The current procedure data 236 contains a synopsis of key donor data, instrument and disposable data, targeted procedure processing values, and actual procedure processing values. FIG. 14 exemplifies the nature and type of information contained in a representative procedure data file 236, in a written report format, as will be described later.

The PROCEDURE DRIVER sends generated procedure data 236 to the FILE SYSTEM task module 224, which processes the data on the storage device 204 in a designated secure file structure for storage, retrieval, and manipulation. Further details of the FILE SYSTEM task module 224 will be described later.

b. Event Data (the E Data)

During the course of the procedure, the PROCEDURE DRIVER task module 222 can also generate other discrete types of data. For example, in the illustrated embodiment (see FIG. 7), the PROCEDURE DRIVER task module 222 periodically generates time stamped event data 238, which together build a chronological record of key processing events.

Event data 238, which, in shorthand, are called "E Data" in FIG. 7, can be generated in response to the occurrence of key events, e.g., marking the start of the procedure, the installation of disposable components, the entry of processing parameters, priming, the entry of data scanned by the bar code scanner 214, alarm conditions and their resolution, and the end of the procedure. Other event data 238 can also be generated periodically (e.g., every 15 minutes) to provide then-current processing parameters, e.g., the volume of whole blood processed, the whole blood flow rate, whole blood inlet pump pressure, red blood cell return pump pressure.

The PROCEDURE DRIVER task module 222 communicates event data 238 to the FILE SYSTEM task module 224. As will be described in greater detail later, the FILE SYSTEM task module 224 incorporates the event data 238 into the designated file structure on the storage device 204. The stored system event data 238, when arranged in chronologic order by file time stamp, comprise a time-order record of significant procedure events and conditions. FIG. 15 exemplifies the nature and type of information contained in a compilation of representative event data files 238, in a written report format, as will be described later.

c. System Condition Data (the S Data)

In the illustrated embodiment (see FIG. 7), during the course of the system operation, system tasks also generate time stamped system condition data 336, which, in shorthand, are $$ called "S Data" in FIG. 7. The system condition data represent preselected states, status, or error conditions relating to the pumps, solenoids, valves, optical detectors, and other functional hardware of the system under the control of the instrument manager 50.

Figure 17:
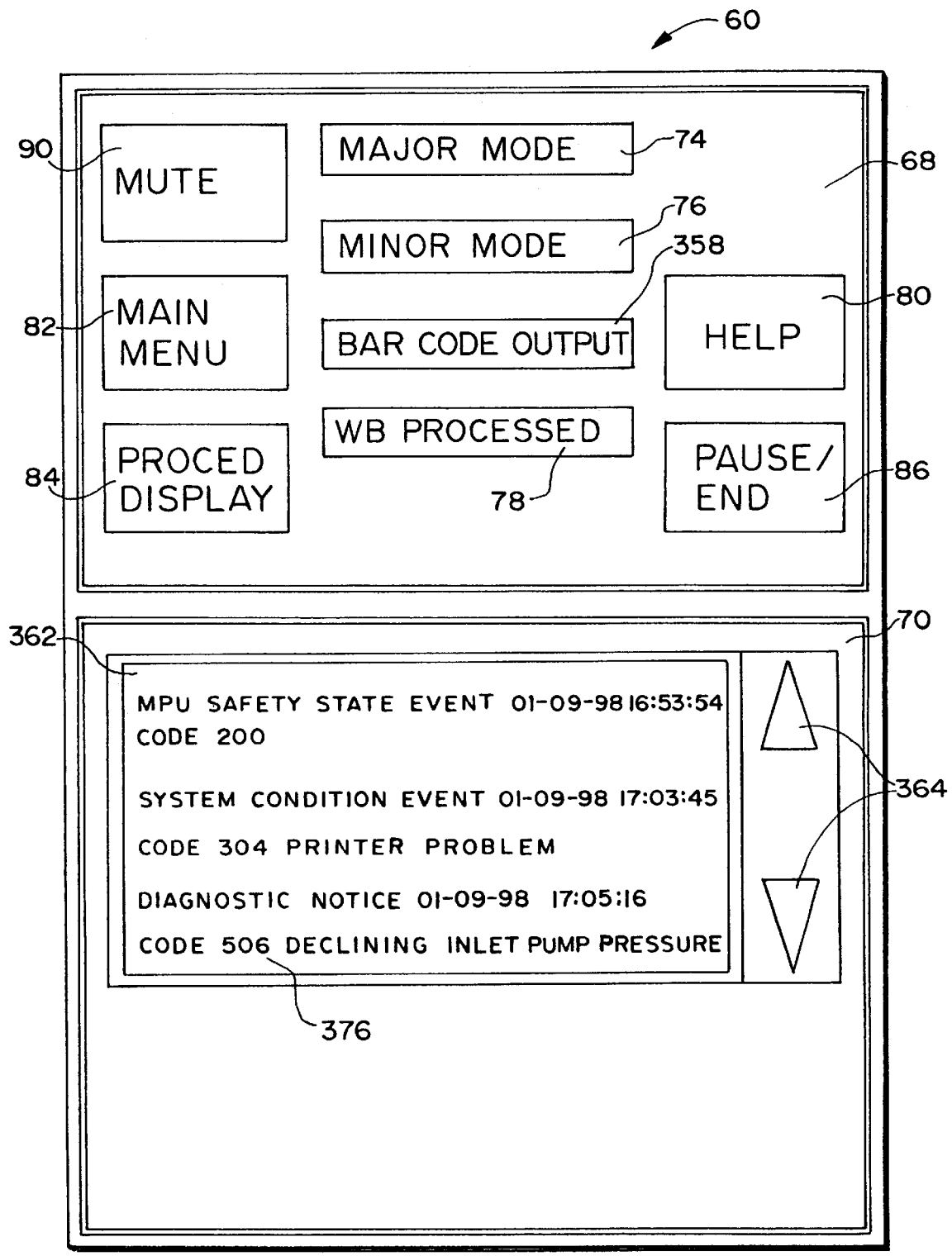
FIG. 17 a view of the dual region interface screen, showing the Log Viewer Submenu in the working region of the interface screen.

The PROCEDURE DRIVER task module 222 communicates system condition data 336 to the FILE SYSTEM task module 224. As will be described in greater detail later, the FILE SYSTEM task module 224 incorporates the system condition data 336 into the designated file structure on the storage device 204. The stored system condition data 336 comprise time-order records of significant system hardware-related conditions during the course of the procedure. FIG. 17 exemplifies the nature and type of information contained in a compilation of representative system condition data 336, when formatted for viewing by an operator, as will be described later.

d. The Dump Sensor Data (the D Data)

In the illustrated embodiment (see FIG. 7), periodically during the course of the procedure (e.g., every 5 seconds), the PROCEDURE DRIVER task module 222 generates discrete time stamped dump sensor data 350, which, in shorthand, are called "D Data" in FIG. 7. The dump sensor data 350 are snapshots of current sensed values recorded by condition sensing hardware coupled to the controller 18. The condition sensing hardware can monitor, e.g., inlet and outlet pump pressures, weights of blood collection containers, and optical transmission values sensed by optical detectors.

The PROCEDURE DRIVER task module 222 communicates dump sensor data 350 to the FILE SYSTEM task module 224. As will be described in greater detail later, the FILE SYSTEM task module 224 incorporates the dump sensor data 350 into the designated file structure on the storage device 204. The dump sensor data 350 comprise a time-order record of sensed conditions monitored during the course of a given procedure.

ii. The File System Task

The FILE SYSTEM task module 224 provides file services for the PROCEDURE DRIVER task module 222, the DATA EXCHANGE task module 228, and the REPORT task module 226. It provides the interface for storage, retrieval, and manipulation of the procedure data 236, the event data 236, the system condition data 336, and the dump sensor data 350.

Figure 8:
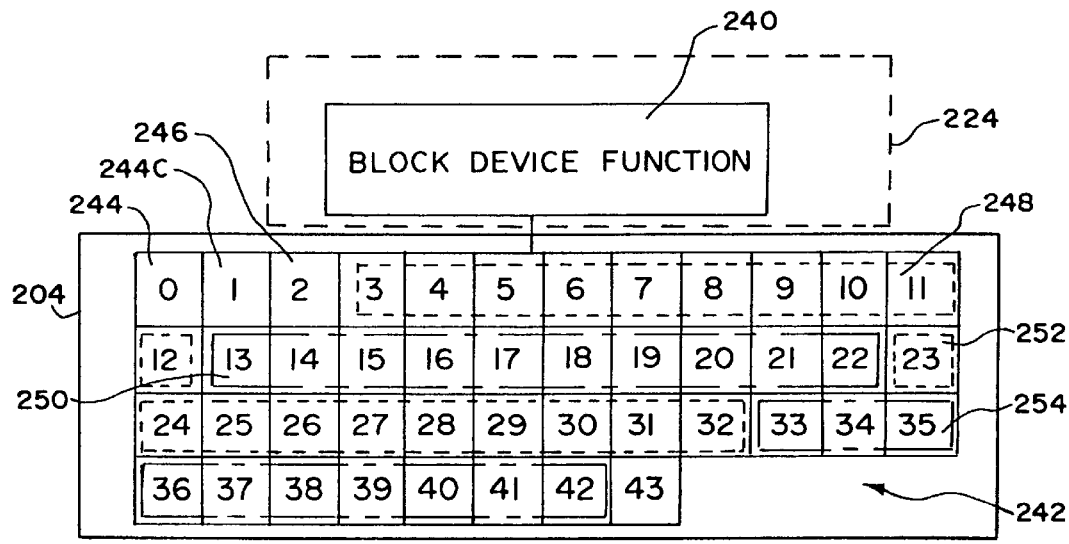
FIG. 8 is a diagrammatic view of the block file structure of the storage device of the data interface shown in FIG. 7.

As FIG. 8 shows, the FILE SYSTEM task module 224 includes a block device function 240. The block device function 240 formats the media 242 of the storage device 204 to have N blocks, each addressable by a number starting from 0 and going up to but not including N (in FIG. 8, N=43). The format structure includes a root node 244, which occupies block 0, with a redundant copy 244C in block 1. The format structure further includes a directory node 246, which occupies one or more blocks beginning with block 2. The format structure allocates the remaining blocks, up to but not including block N, as space for the various data 236, 238, 336, and 350 generated by the PROCEDURE DRIVER task module 222.

The block device function 240 statically divides the remaining blocks into discrete file spaces, which are each allocated to accept one type of data 236, 238, 336, or 350. FIG. 8 shows, for the purpose of illustration, four file spaces 248, 250, 252, and 254, for the four types of data 236, 238, 336, and 350, respectively. However, there are typically more blocks available, and additional file spaces can therefore be allocated.

Each file space 248, 250, 252, and 254 comprises a contiguous range of blocks. In the illustrated embodiment (FIG. 8), each file space 248, 250, 252, and 254 has, for the purpose of illustration, the same maximum size of 10 blocks. However, the data 236, 238, 336, and 350 will impose different size requirements, and the file spaces 248, 250, 252, and 254 will typically have different maximum sizes.

a. The Root Node

The root node 244 identifies the name of file system and describes the overall layout geometry imposed by the runtime code. The root node 244 specifies the total capacity of the file system in blocks and the maximum number of fixed size files that may be used, i.e., how many statically allocated file spaces exist (which, in the illustrated embodiment, is four). The root node 244 also includes a copy of the template that was used by the PROCEDURE DRIVER task module 222 to create the procedure data 236. The template is stored in the root node 244 principally for informational purposes. Still, the stored template could be used as a reference to reconstruct the file system, should radical damage occur.

The root node 244 contains no modifiable information. It is never modified once the file system is created. An identical copy 244C of the root node 244 is kept in block 1, in case block 0 becomes unreadable.

b. The Directory Node

After the media 242 has been formatted by the block device function 240, it has the ability to accommodate a fixed number of files spaces, each having a fixed maximum predetermined size. The directory node 246 comprises a directory table 256 for the formatted file spaces 248, 250, 252, and 254.

Figure 9:
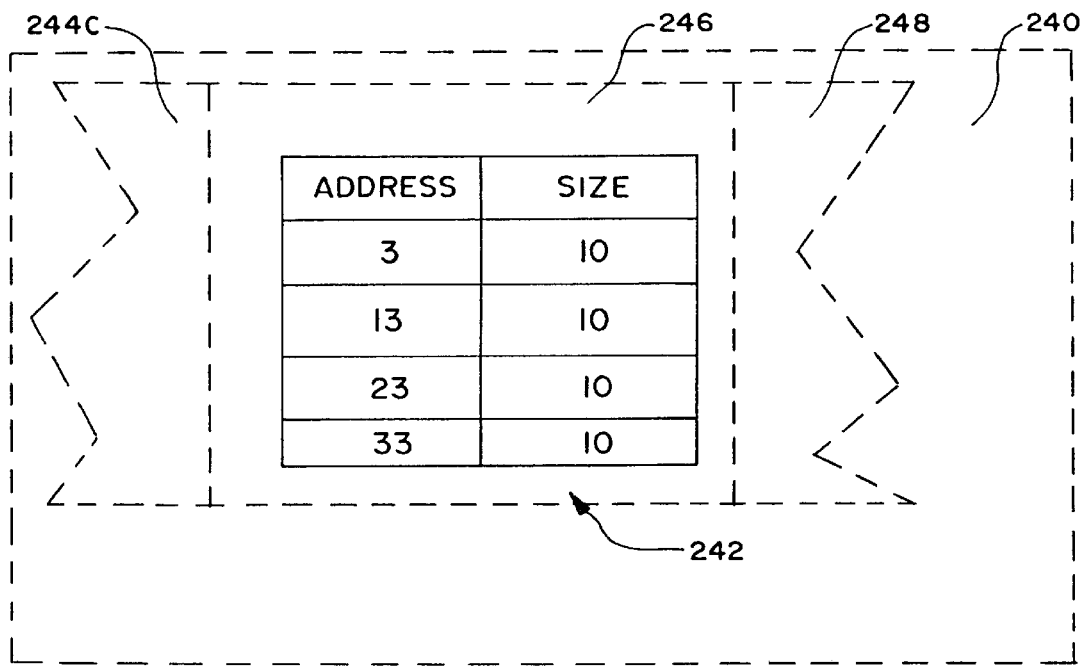
FIG. 9 is a diagrammatic view of the directory table of the block file structure shown in FIG. 8.

As exemplified in FIG. 9, the directory table 256 lists the starting block address and fixed size of each file space. The table 256 includes a directory element 258, or "slot," for every preallocated file space in the file system (of which there are four in the illustrated embodiment). Each directory element 258 contains the block number (i.e., address) of a preallocated file space and the preallocated size of the file space in units of blocks.

As described herein, the block numbers or addresses retained in the directory table 256 refer to the logical file system block addresses, which may or may not correspond to physical media block addresses.

The directory table 256 contains only one directory level, i.e., the directory table 256 is not hierarchical. The directory table 256 also is not dynamic. It is never modified once a file system has been created. The table 256 serves simply to provide static pointers to the location of the allocated file spaces.

The directory table 256 also does not indicate whether or not a preallocated file space contains data or is available. Dynamic allocation information is kept on the byte-stream data written to the file spaces, i.e., the presence or absence of data itself provides the allocation information for the file space.

The FILE SYSTEM task module 224 as described retains the integrity of the block file system structure, despite power failure or arbitrary corruption of data on the storage device 204. In the face of such abuse, the FILE SYSTEM task module 224 will not lose the basic block structure of the file system, nor will it require a distinct file system repair operation to be performed. Each file space 248, 250, 252, and 254 has a fixed maximum size, and the file space cannot grow to accommodate more data. Any allocation of file spaces inconsistent with the directory table 256 can be fixed on the fly.

The block device function 240 also includes a hard safety check that does not allow writes to block numbers less than the first preallocated file space, once the file system has been created. The low-numbered blocks are only activated for writing during file system creation. Therefore it is unlikely that a software bug could destroy the directory blocks. Since the directory blocks are static, it is also unlikely they could be destroyed by a write error during power failure.

c. Data Spaces

Figure 10:
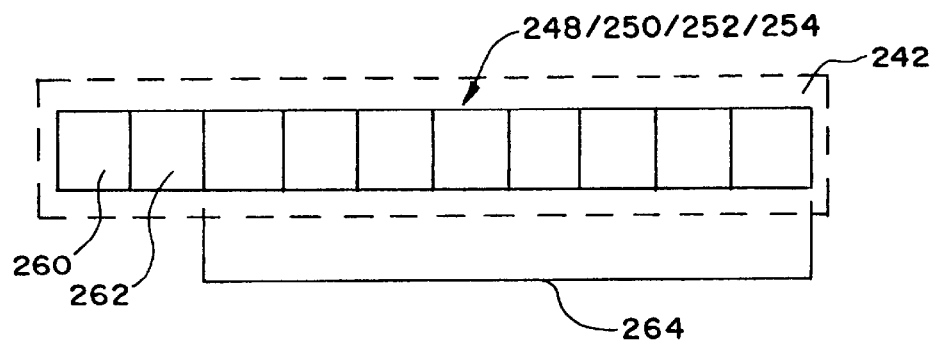
FIG. 10 is a diagrammatic view of one block file space allocated in the block file structure shown in FIG. 8.

As FIG. 10 shows, each file space 248, 250, 252, and 254 includes a primary node 260. The primary node 260 contains metadata associated with the file space (i.e. allocated or free, file name, creation time, current size, etc.). Each file space also includes a secondary node 262. The secondary node 262 has the same contents as the primary node 260. This is used for "flip-flopping" while updating a file's metadata, as will be described later.

Each file space 248, 250, 252, and 254 also includes the files's preallocated physical space 264. The space 264 accepts the data contents of allocated procedure data 236, event data 238, system condition data 336, or dump sensor data 350.

The block device function 240 performs no random access writes. The block device function 240 allows either the reading and writing of whole blocks addressed by beginning block number, or the successive appending of data forward in the file space until the file space is filled.

As implemented in the illustrated embodiment, at the outset of a given procedure, one file space 248 is reserved for the procedure data 236 generated during the procedure, and one file space 250 is reserved for all event data 236 generated during the procedure. Upon the first boot-up of the data interface 202, one file space 252 is designated for system condition data 336 for all subsequent procedures, and one file space 254 is designated for dump sensor data 350 for all subsequent procedures. As will be described in greater detail later, the file spaces 252 and 254 hold ringfiles, to which the newest designated data 336 and 350 are appended, overwriting the oldest data.

(1) The Procedure Data File Space

The maximum size of the reserved procedure data file space 248 is selected to comfortably accommodate the entire template of the procedure data 236, plus a backup copy (as described later). In a representative embodiment, a maximum file size of about 5.6 kilobytes is reserved.

The reserved procedure data file space 248 receives the first procedure data 236 generated by the PROCEDURE DRIVER task module 222 at the outset of a procedure. Subsequent procedure data 236 generated by the PROCEDURE DRIVER task module 222 during the course of the procedure are written as a block to the same procedure file space 248, beginning at logical offset zero of the file space 248, thereby overwriting the preceding procedure data in its entirety. Conceptually, the procedure data 236 in the file space 248 is periodically "refreshed" as the procedure progresses, until the procedure ends, which leaves the last-written procedure data 236 in the space 248.

(2) The Event Data File Space

The maximum size of the reserved event data file space 250 is selected to comfortably accommodate all event data 238 generated during a typical procedure, plus backup copies (as described later). In a representative embodiment, a maximum file size of about 66.5 kilobytes is reserved.

The reserved event data file space 250 receives at logical offset zero, the first event data 238 generated by the PROCEDURE DRIVER task module 222 at the outset of a procedure. The next event data 238 is appended at the end of file (EOF) point of the first event data 238. Successive event data 238 are appended in this fashion, until physical data space 250 is filled, after which no more event data can be recorded for the procedure.

Should the data space 250 fill to its fixed capacity, the FILE SYSTEM task module 224 generates a message output to the USER INTERFACE task module 230 (to be described later). The assessment of the maximum size of the event data file space 250 should be carefully made, to assure that event data are not lost near the end of a given procedure. The block device function 240 can, as a back up, also include a function that designates a second event file space, should an atypical procedure occur that generates an atypical number of event data to fill the first event file space 250.

(3) The System Condition Data File Space and the Dump Sensor File Space (Ringfiles)

In like fashion, the block device function 240 writes and successively appends system condition data 336 and dump sensor data 350 in the designated reserved file spaces, respectively, 252 and 254. However, unlike the file space 250, which allows no further data entry when its physical data space is filled, the block device function 240 includes a function 266 that accommodates continuous appending of system condition data 336 and dump sensor data 350 in their respective fixed file spaces 252 and 254. The function 266 treats the fixed physical allocated space 264 for these spaces 252 and 254 as a circular ring, or ringfile 268 (see FIG. 11). In a ringfile 268, the oldest data 270 is overwritten with new data 272 after the file space 264 is filled.

Figure 11:
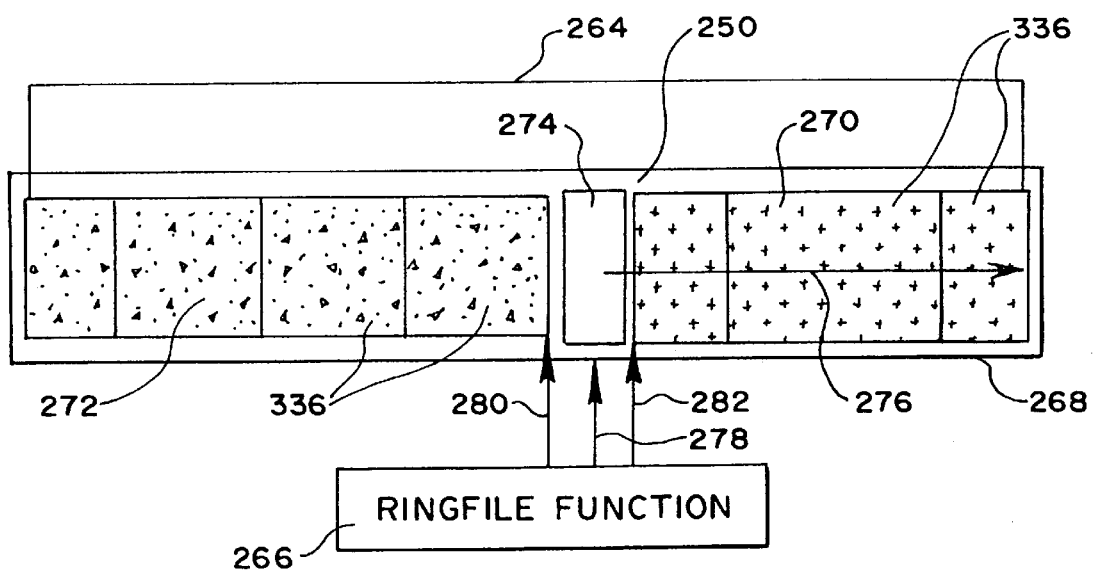
FIG. 11 is a diagrammatic view of the ringfile function, which controls the writing of data into the block file space shown in FIG. 10.

The ringfile function 266 initially appends all data (which, for the purpose of illustration in FIG. 11, are system condition data 336) generated by the PROCEDURE DRIVER task module 222 during a given procedure in the designated file space 264. As the data 336 are successively written to the designated file space 264, the size of the ringfile 268 starts at zero for the first data 336 and grows as additional data 336 are appended, until the file space 264 becomes full. At this point (see FIG. 11), the ringfile function 266 "wraps" the data by overwriting old data 270 with new data 272 beginning at the first node allocated to data in the file space 264 (that is, after the primary and secondary nodes 260 and 262, which carry the metadata).

A ringseam 274 separates the oldest data 270 in the file space 264 and the newest data 272 in the file space 264. As new data 272 enters the file space 264, the ringseam 274 continuously moves toward the end of the preallocated space (as indicated by arrow 276 in FIG. 11). Once the end of the file space 264 is reached, the ringseam 274 wraps around to first data node and again moves forward toward the end of the file space 264.

Following the first wrap of data in the file space 264, the ringfile function 266 maintains a logical ringseam pointer 278. The ringseam pointer 278 marks the block address of the ringseam 274. The ringfile function 266 also locates the file's logical end-of-file pointer 280 at the block address that marks the logical junction between the newest data 272 and the ringseam pointer 278. The ringseam function 266 also places the logical offset zero pointer 282 at the block address that marks the logical junction between the oldest data 270 and the ringseam pointer 278. Following the first wrap of data, the ringseam function 266 appends data beginning at the logical end of file pointer 280. As the appended data is written to the file space 264, the ringseam function 266 advances the logical offset zero pointer 282 in tandem with the ringseam pointer 278.

The fixed maximum size of the system condition data file space 252 and dump sensor data file space 254 are selected to comfortably accommodate an expected compilation of data, plus backup copies (as described later). In a representative embodiment, a maximum file size of about 100 kilobytes is reserved for the system condition data file space 252, and a maximum file size of about 1 megabytes is reserved for the dump sensor data file space 254.

(4) File Space Integrity

The block device function 240 automatically creates backup copies of the data 236, 238, 336, and 350 written to the respective file spaces 248, 250, 252, and 254. Furthermore, data structures in all allocated file spaces are protected per-block by a 16-bit CRC. This allows the block device function 240 to detect if a block was successfully written and whether it is valid when read back. If a block is found to be invalid for any reason, including a CRC mismatch, the block device function 240 verifies the backup copy of the block. If valid, the block device function 240 proceeds using the data in the backup copy, or the backup data can be used to repair the damaged block.

The most dynamic aspect of the file system is the file node 260 of a given file space. Whenever data is appended to a file space, or written to a file space, the metadata of the file space must be updated. The last modified time must be updated to the current time. If appended, the logical size of the file must be increased by the amount of data appended. The current read or write position must also be updated to indicate where the next read or write operation should occur.

Because the file node 260 is updated so frequently, and because a file node 260 is crucial when accessing a file, each file space 248, 250, 252, and 254 includes the secondary file node 262. Each file node 260 and 262 has an "age" marker, which is initialized at zero when a new file is created in the file space. Each time the file node 260 and 262 of the file space is modified, the file node's age marker is incremented.

Whenever a file's metadata must be updated, the block driver function 240 registers the file node's age marker. If the age marker is an even number, the primary file node 260 is modified. Conversely, if the age marker is an odd number, the secondary file node 262 is modified. Writes to the file nodes 260 and 262 are thereby "flip-flopped" between the primary and secondary file nodes 260 and 262.

When the device block function needs to read a file node, it reads both primary and secondary file nodes 260 and 262 and considers the one with the highest "age" marker to be valid. This allows a file node update operation (i.e. a write to a file node) to experience a hardware failure, in which the entire file node is destroyed. The alternate file node will always contain a consistent, albeit older, state of the file.

The ability to withstand abuse does not extend to data contained in each procedure or event data 236 or 238. It is the responsibility of the PROCEDURE DRIVER task module 222 and FILE SYSTEM task module 224 to maintain data integrity. However, as a general rule, data loss will occur at the tail of the file when it is appended in a forward direction. Thus, should an error occur in an append operation, it affects only the most recently appended data, which represents a relatively small portion of the overall file.

The FILE SYSTEM task module 224 maintains file integrity without resort to conventional complex data base management functions, such as journalling-file systems, or a commit-rollback transaction facility. By not allowing formatted file spaces to grow, the FILE SYSTEM task module 224 requires only small modifications to the file system metadata as data is written. The FILE SYSTEM task module 224 does not rely upon a file directory that dynamically points to where each file is located. The FILE SYSTEM task module 224 does not move blocks that contain file system data and then update pointers to refer to their new location. The FILE SYSTEM task module 224 does not dynamically extend the size of the file by removing blocks from a free pool and attaching them to the file, or dynamically return a file's blocks to the free pool and unlinking the file from the file directory. The FILE SYSTEM task module 224 minimizes the windows of time during which the file system is being dynamically altered, and during which time a file system is vulnerable to catastrophic data corruption due to power failure. By minimizing the time of vulnerability, the FILE SYSTEM task module 224 minimizes the chance of catastrophic corruption of data, should power failure occur.

iii. The User Interface Task (File System Task Support)

The USER INTERFACE task module 230 links the FILE SYSTEM task module 224 and the REPORT task module 226 to the interface manager 66, which has been previously described. The USER INTERFACE task module 230 sends to the interface manager 66 abstract Create_Display# commands prescribed to support the data interface 202. The interface manager 66 processes the data interface 202 Create_Display# commands to generate specific Format_Display# commands. As before described the Format_Display# commands control the particular format, attributes, and protocols necessary to create, refresh, and close the visual display on the interface screen 60. The USER INTERFACE task module 230 thereby provides the data interface 202 with a graphical user interface.

Figure 6A:
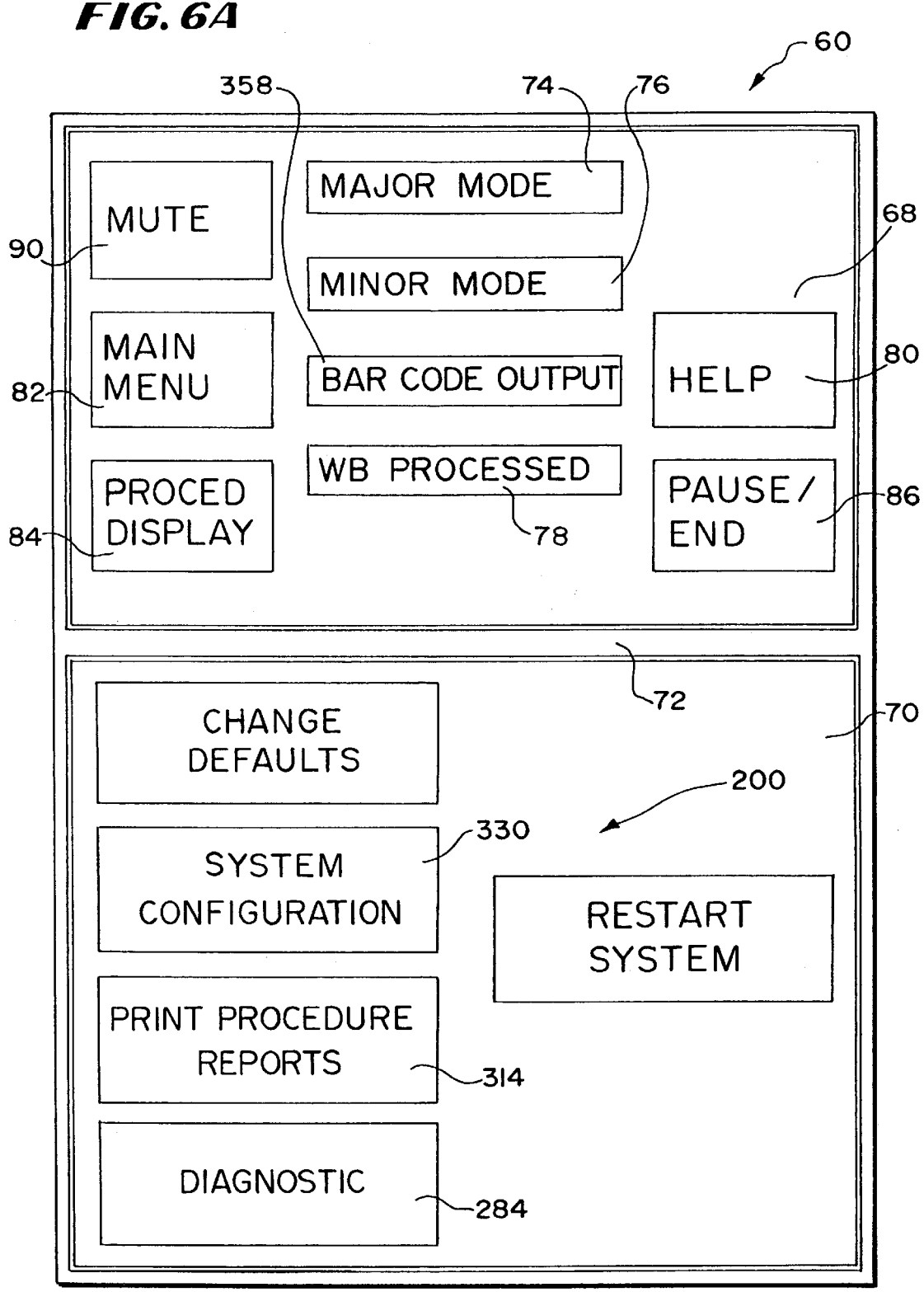
FIG. 6A a view of the dual region interface screen, showing the Special Features Submenu in the working region of the interface screen.

In the illustrated embodiment (see FIG. 4), the Main Menu display shown by default in the working region 70 of the screen 60 includes a SPECIAL FEATURES button field 96. When touched, the SPECIAL FEATURES button field 96 calls up a function that displays a Special Features Submenu in the working region 70, as FIG. 6A shows. The Features Submenu lists in an array of touch selectable button fields 200. One of the button fields 284 on the Special Features Submenu is labeled DIAGNOSTIC.

Figure 6B:
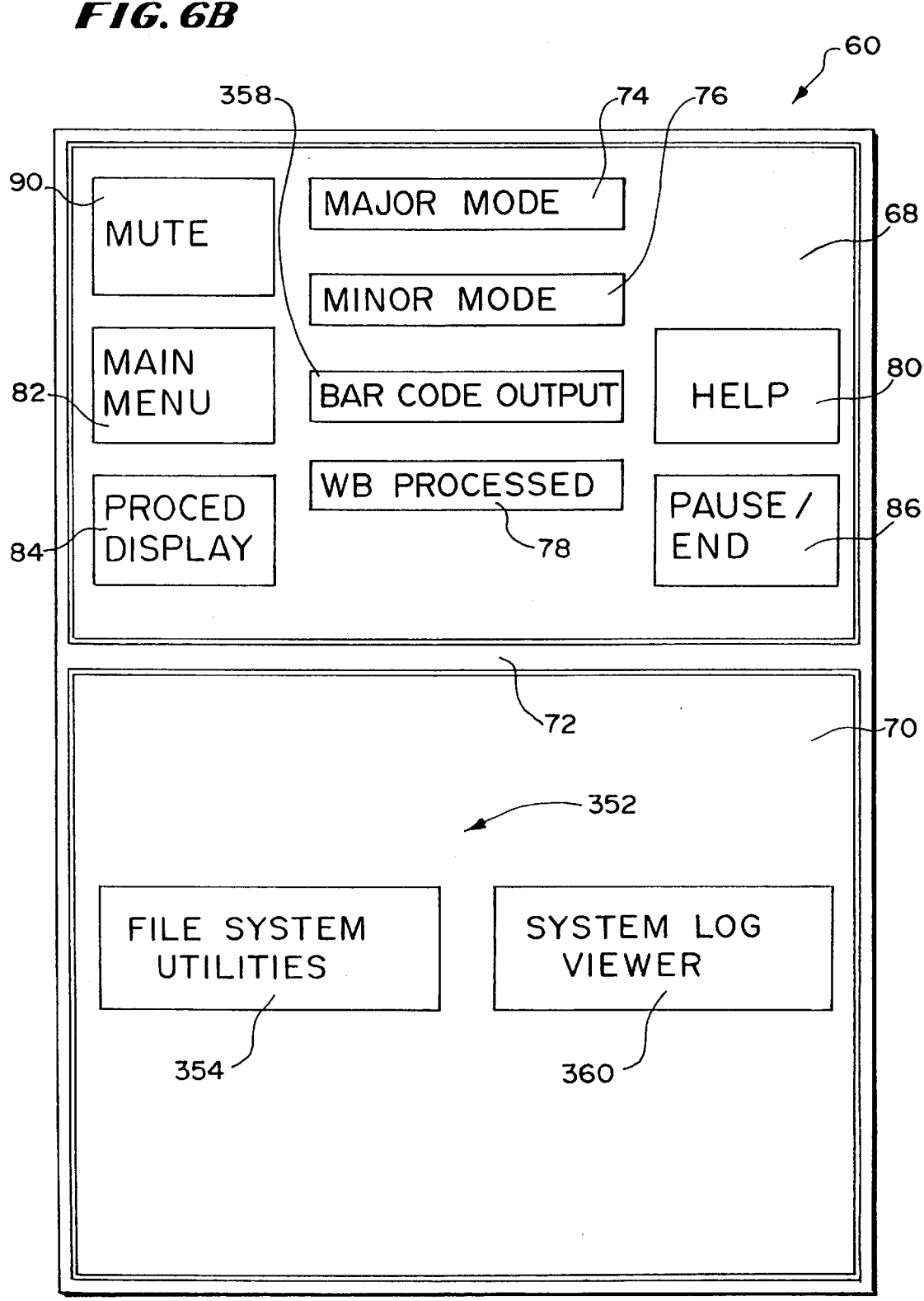
FIG. 6B a view of the dual region interface screen, showing the File Manger Submenu in the working region of the interface screen.

When DIAGNOSTIC button field 284 is pushed, the USER INTERFACE task module 230 generates a prescribed Create_Display# command to the interface manager 66, which, in turn, generates a Format_Display# command to display a File Manger Submenu in the working region 70, as FIG. 6B shows.

The File Manager Submenu lists in an array of touch selectable button fields 352. One of the button fields 354 is labeled FILESYSTEM UTILITIES.

a. Filesystem Utilities

Figure 12:
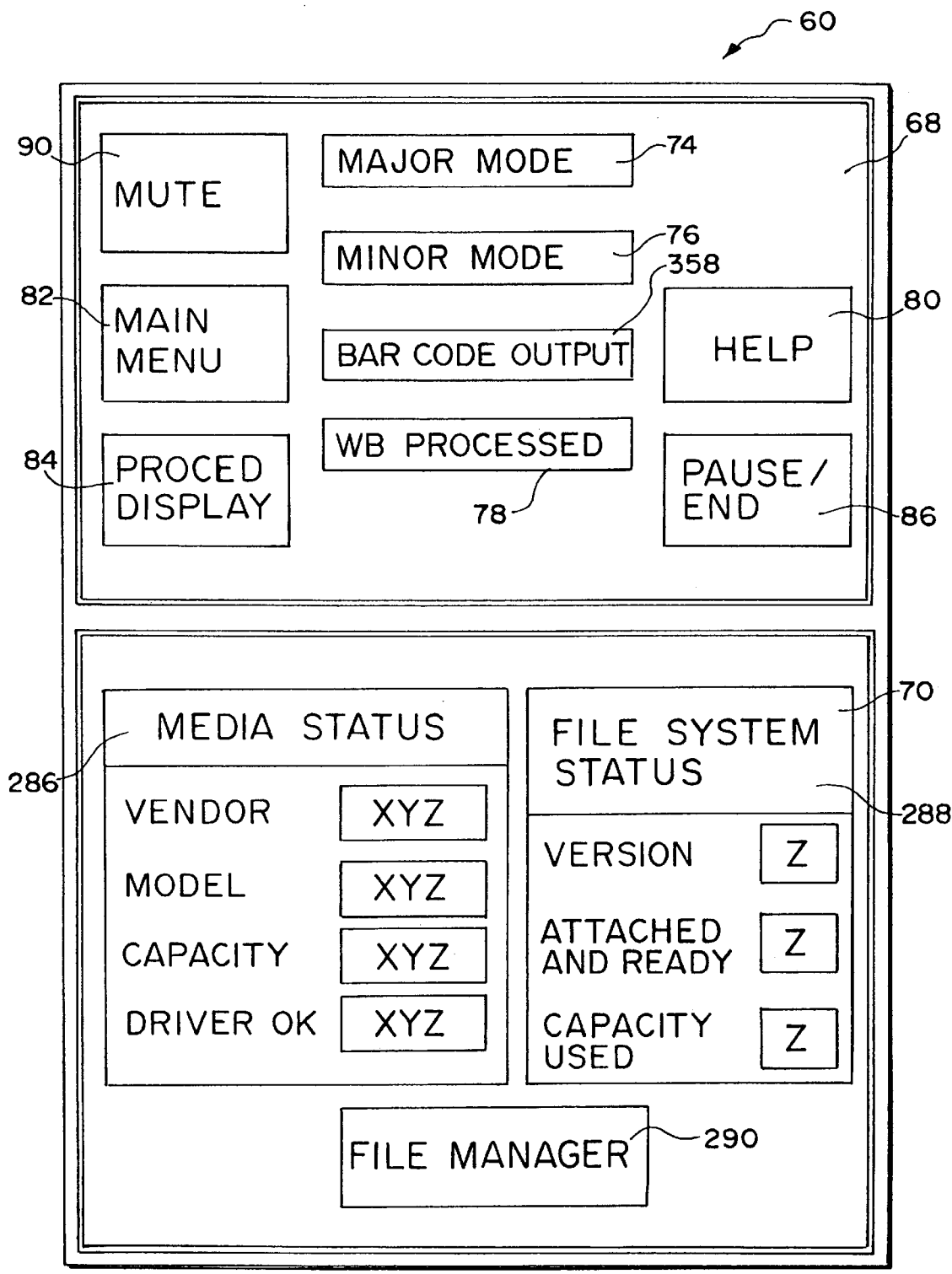
FIG. 12 a view of the dual region interface screen, showing the File System Information Submenu in the working region of the interface screen.

When the FILESYSTEM UTILITIES button field 354 is pushed, the USER INTERFACE task module 230 generates a prescribed Create_Display# command to the interface manager 66, which, in turn, generates a Format_Display# command to display a File System Information Submenu, as shown in FIG. 12.

The File System Information Submenu includes a first box 286, which identifies the attributes of the storage device 204 of the data interface 202, e.g., by vendor, model, capacity, and by confirming its installation. This information is provided to the USER INTERFACE task module 230 by the FILE SYSTEM task module 224. The File System Information Submenu also includes a second box 288, which identifies the attributes of the FILE SYSTEM task module 224 itself, e.g., by identifying the software version of the FILE SYSTEM task module 224 which is installed, by confirming its operational readiness, and by listing its present capacity.

Figure 13:
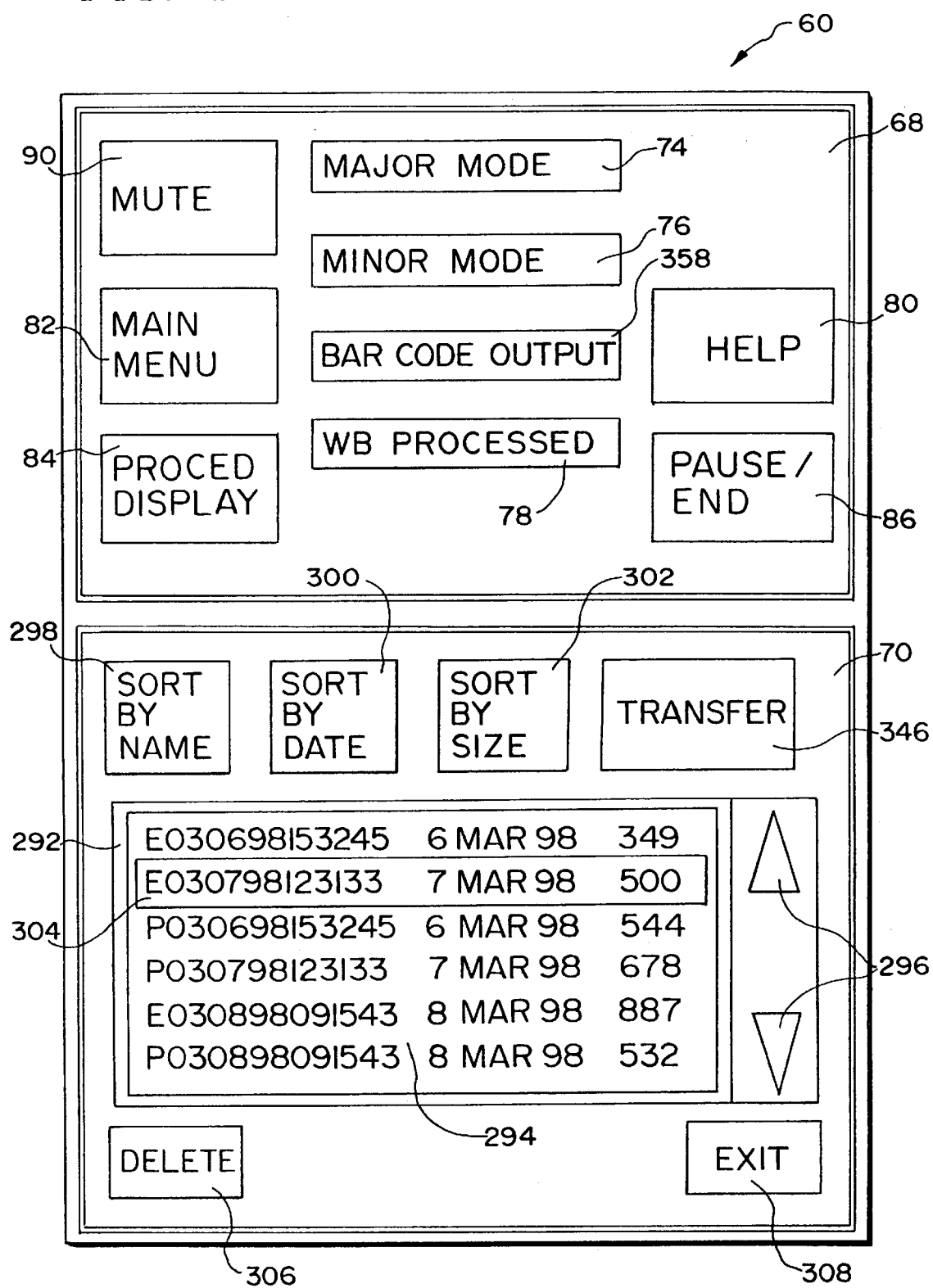
FIG. 13 a view of the dual region interface screen, showing the File Directory Submenu in the working region of the interface screen.

The File System Information Submenu also includes a push button field 290 labeled FILE MANAGER. When the FILE MANAGER button field 290 is pushed, the USER INTERFACE task module 230 generates a prescribed Create_Display# command to the interface manager 66, which, in turn, generates a Format_Display# command to display a File Directory Submenu, as FIG. 13 shows.

The File Directory Submenu includes a box field 292. The USER INTERFACE task module 230 commands the FILE SYSTEM task module 224 to read the current metadata file node 260 or 262 of each allocated procedure file space 248 and event file space 250. The USER INTERFACE task module 230 formats the metadata into file system data 294, which is listed in rows in the box field 292 by E (Event Data) or P (Procedure Data) suffix, time stamp, and file size residing in the storage device 204. The operator can scroll using control buttons 296, up and down the rows in known fashion.

The File Directory Submenu also includes sort-option push button fields 298, 300, and 302, labeled, respectively, SORT BY NAME, SORT BY DATE, and SORT BY SIZE. When a sort-option is selected, the USER INTERFACE task module 230 reformats the listing in the box field 292 to arrange the file order accordingly, by name, by date, or by size.

The USER INTERFACE task module 230 commands the display of a highlight 304 in the File Directory Submenu to allow a user to select a file row. The File Directory Submenu includes a DELETE push button field 306. When the DELETE button field 306 is pushed, the USER INTERFACE task module 230 commands the FILE SYSTEM task module 224 to delete the data contents of the highlighted file space from the storage device 204. This frees the file space for receiving data for another procedure.

Figure 4:
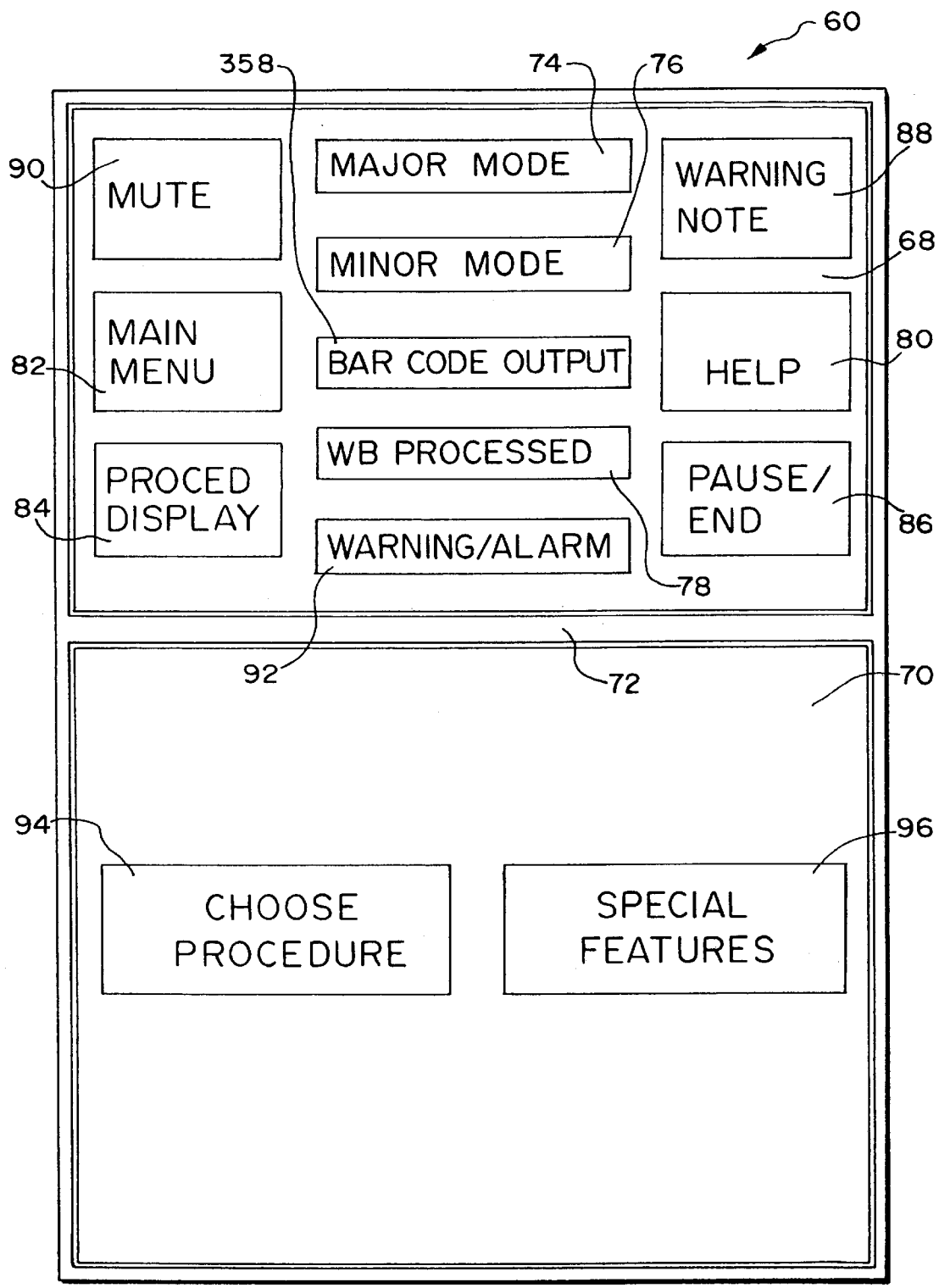
FIG. 4 is a view of the dual region graphical user interface screen, showing the block and touch activated fields that the interface screen contains, and also showing the Main Menu in the working region of the interface screen.

The File Directory Submenu also includes an EXIT push button field 308. When the EXIT button field 308 is pushed (or whenever the MAIN MENU button field 82 visible in the status region 68 is pushed), the USER INTERFACE task module 230 returns the display in the working region 70 back to the default Main Menu, as shown in FIG. 4.

b. System Log Viewer

Another button field 360 on the File Manager Submenu is labeled SYSTEM LOG VIEWER. When the SYSTEM LOG VIEWER button field 360 is pushed, the USER INTERFACE task module 230 generates a prescribed Create_Display# command to the interface manager 66, which, in turn, generates a Format_Display# command to display a Log Viewer Submenu, as shown in FIG. 17.

The Log Viewer Submenu includes a box field 362. The USER INTERFACE task module 230 commands the FILE SYSTEM task module 224 to read the system condition data 336 contained in the allocated ringfile space 252. The USER INTERFACE task module 230 formats the system condition data 336 to display their contents in chronological order by row in the box field 362. Each row lists, e.g., a description of the state, condition, or error recorded, with a time stamp, and an identifying system reference code. Other information contained in the data 336 can also be listed. The operator can scroll using control buttons 364, up and down the rows in known fashion.

When the MAIN MENU button field 82 visible in the status region 68 is pushed, the USER INTERFACE task module 230 returns the display in the working region 70 back to the default Main Menu, as shown in FIG. 4.

c. Bar Code Display

While the USER INTERFACE task module 230 issues commands to change the working region 70 of the screen 60 to display file directory information and functions (FIGS. 12 and 13), or the system condition event log (FIG. 17), the status region 68 of the screen 60 continues to simultaneously show its information. The MINOR MODE field 76 continues to show that the procedure is in the collection mode, and the status region continuously shows in the WB PROCESSED FIELD 78 the volume of WB drawn from the donor. The location and attributes of the other button fields 80/82/84/86 remain unchanged, unless the procedure changes operational mode, at which time the MINOR MODE field 76 will change to reflect this mode change.

Figure 20:
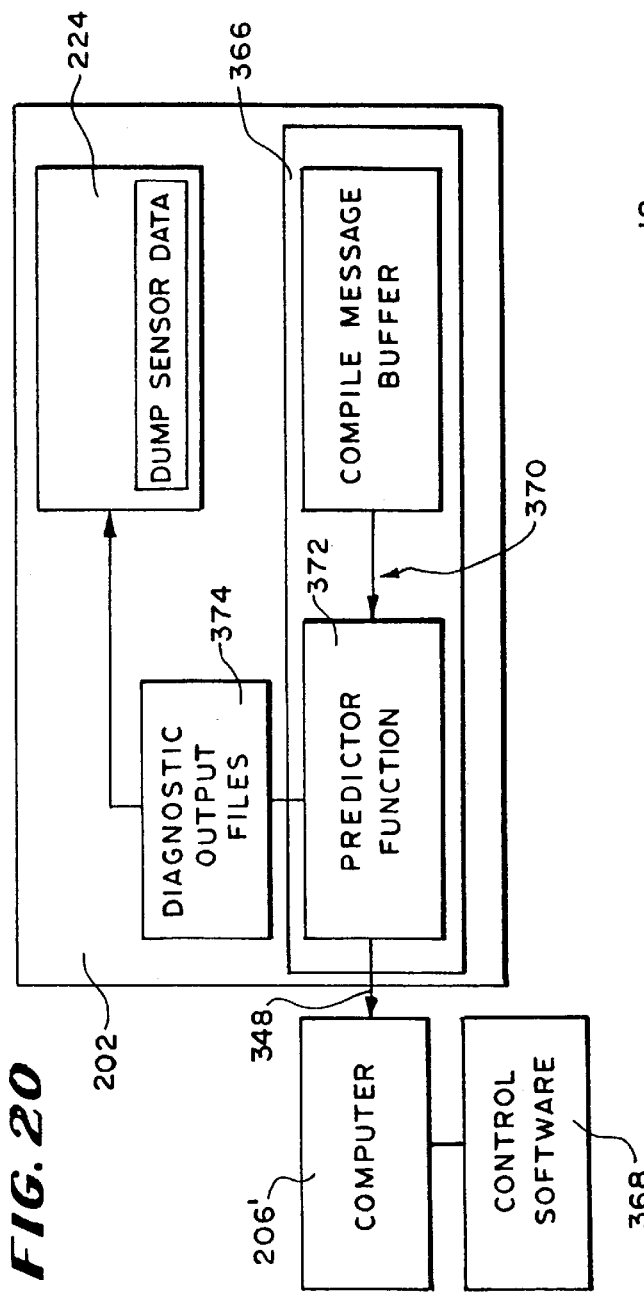
FIG. 20 is a schematic view of the predictor function of the data interface.

The USER INTERFACE task module 230 also communicates with the BAR CODE task module 220. The USER INTERFACE task module 230 receives the feedback message 232 generated by the BAR CODE task module 220 upon confirming acceptance of bar code-scanned input (see FIG. 7). As FIGS. 12, 13, and 20 show, the USER INTERFACE task module 230 commands the display of the feedback message in the a BAR CODE field 358 provided in the status region 68 of the screen 60.

iv. The Report task

The REPORT task module 226 communicates with the printer port link 212. The REPORT task module 226 is serviced by the FILE SYSTEM task module 224 and the USER INTERFACE task module 230. When active, the REPORT task module 226 directs the FILE SYSTEM task module 224 to locate and read designated procedure and event data 236 and 238 then-residing in the storage device 204. The REPORT task module 226 builds reports presenting the data in prescribed alpha-numeric format, which FIGS. 14 and 15 exemplify. The REPORT task module 226 downloads the report to the printer 216.

The format and contents of printed reports can, of course, vary. For example, the REPORT task module 226 can generate a Procedure Report 310 (see FIG. 14), which is built upon a procedure data 236 contained in a given procedure data file space 248 on the storage device 204. As another example, the REPORT task module 226 can generate an Event Report 312 (see FIG. 15), which lists in time order the contents of the event data stored in a given event data file space 250 on the storage device 204.

v. The User Interface Task (Report Task Support)

Figure 16:
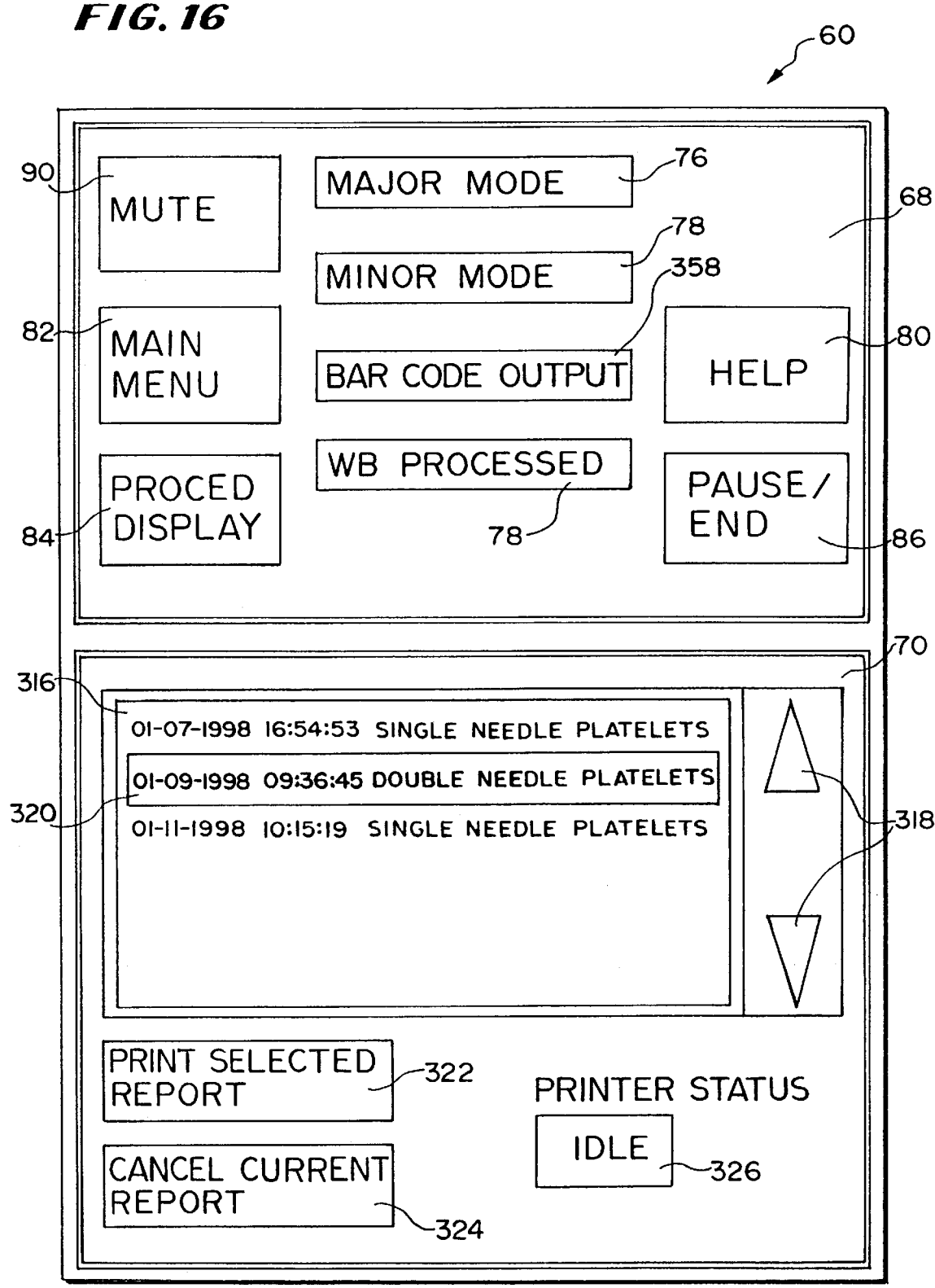
FIG. 16 a view of the dual region interface screen, showing the Print Procedure Reports Submenu in the working region of the interface screen.

The USER INTERFACE task module 230 also links the REPORT task module 226 to the interface manager 66. In the illustrated embodiment, one of the button fields 314 on the Special Features Submenu (see FIG. 6A) (which is accessed through SPECIAL FEATURES button field 96 on the Main Menu display, shown in FIG. 4) is labeled PRINT PROCEDURE REPORTS. When the PRINT PROCEDURE REPORTS button field 314 is pushed, the USER INTERFACE task module 230 generates a prescribed Create_Display# command to the interface manager 66, which, in turn, generates a Format_Display# command to display a Print Procedure Reports Submenu, shown in FIG. 16.

The Print Procedure Reports includes a box field 316, which lists by row the procedures for which current procedure and event data 236 and 238 reside on the storage device 204. The operator can scroll using control buttons 318, up and down the rows in known fashion. The USER INTERFACE task module 230 displays a highlight 320 to make a selection.

The Print Procedure Reports Submenu includes a PRINT SELECTED REPORT push button field 322. When pushed, the USER INTERFACE task module 230 commands the REPORT task module 226 to format and print the formatted reports for the selected procedure (which, in the illustrated embodiment, are the Procedure Report 310 shown in FIG. 14 and the Event Report 312 shown in FIG. 15. By selected a CANCEL CURRENT REPORT push button 324 field, the user can terminate printing of the selected reports.

The Print Procedure Reports Submenu also includes a Printer Status box field 326. The Printer Status box field 326 displays information from the COMMUNICATION MANAGER task module 218 that reports status of the printer 216, e.g., Idle, Busy, Error.

When the MAIN MENU button field 82 visible in the status region 68 is pushed, the USER INTERFACE task module 230 returns the display in the working region 70 back to the default Main Menu, as shown in FIG. 4.

Figure 18:
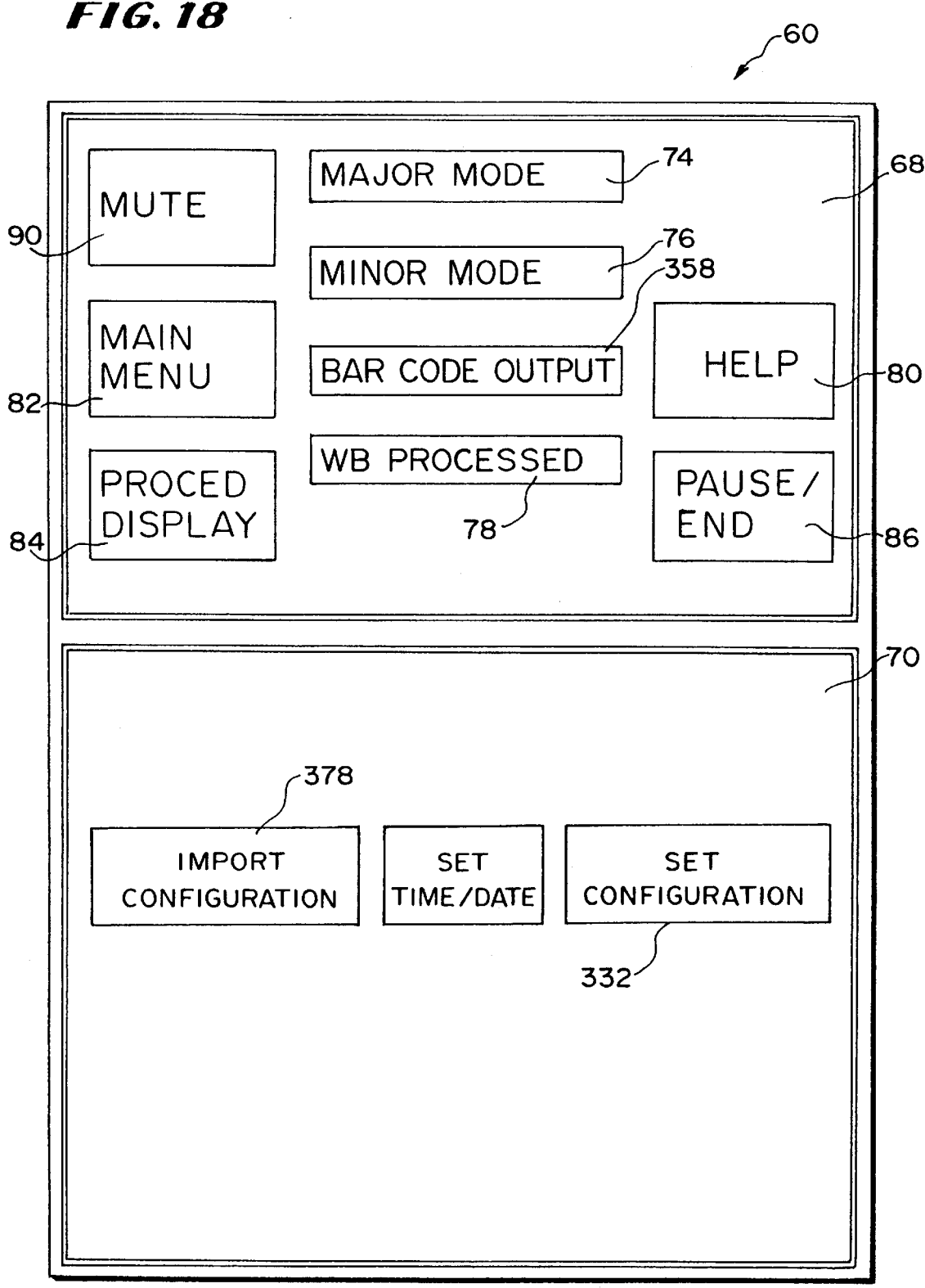
FIG. 18 a view of the dual region interface screen, showing the System Configuration Submenu in the working region of the interface screen.
Figure 19:
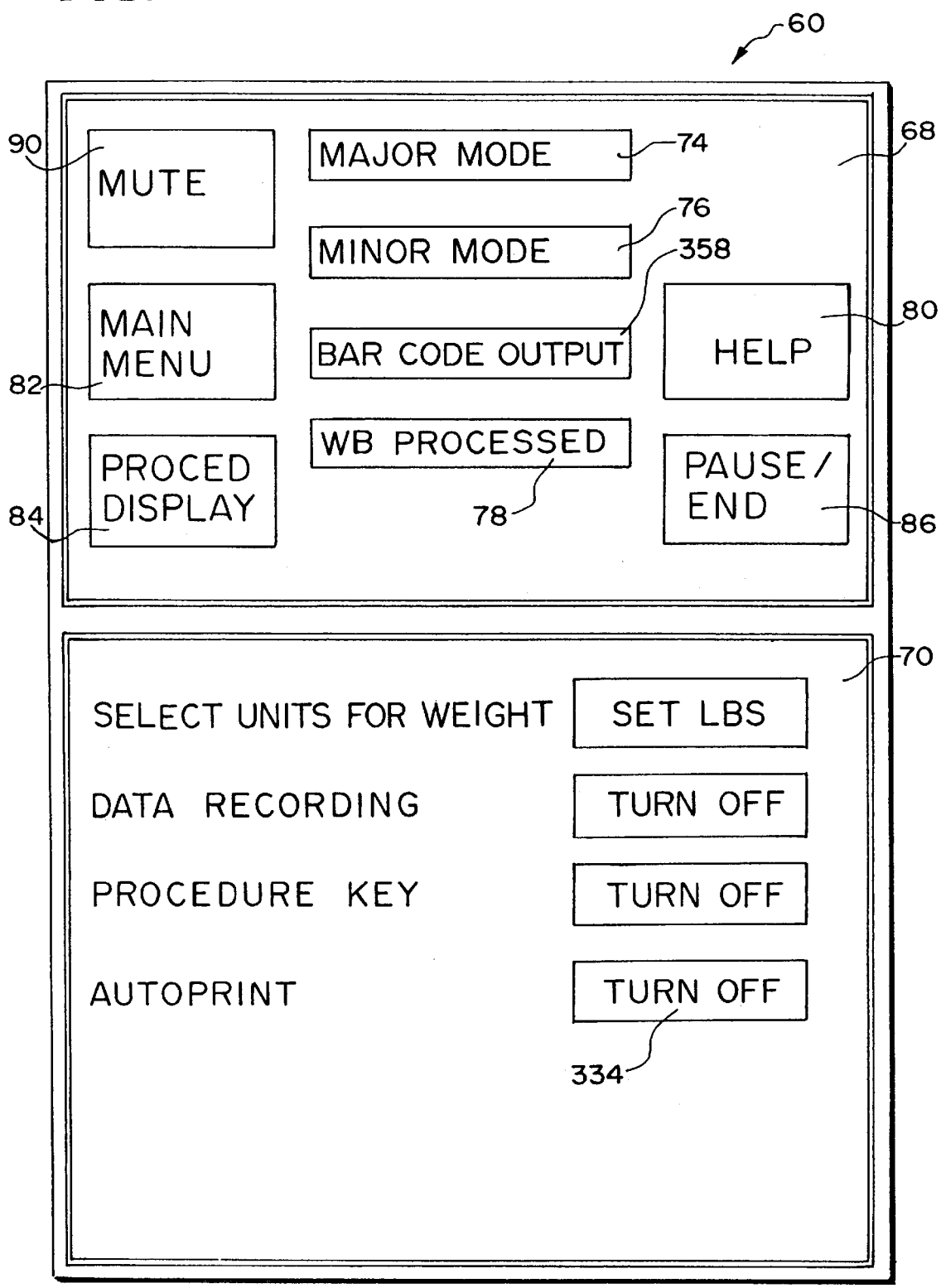
FIG. 19 a view of the dual region interface screen, showing the Set Configuration Submenu in the working region of the interface screen.

The USER INTERFACE task module 230 also allows the operator to condition the REPORT task module 226 to automatically compile and print the Procedure Report 310 and Event Report 312 at the conclusion of a procedure. In the illustrated embodiment (see FIG. 6A), one of the button fields 330 on the Features Submenu is labeled SYSTEM CONFIGURATION. When the SYSTEM CONFIGURATION button field 330 is pushed, the USER INTERFACE task module 230 generates a prescribed Create_Display# command to the interface manager 66, which, in turn, generates a Format_Display# command to display a System Configuration Submenu, as shown in FIG. 18. The System Configuration Submenu, in turn, includes a SET CONFIGURATION button 332, which, when pushed, causes the display of a Set Configuration Submenu, as shown in FIG. 19. The Set Configuration Submenu includes an "AutoPrint" push button field 334. Pushing the button 334 toggles the button label between Turn On and Turn Off.

When toggled to the Turn Off state (in which the autoprint feature is actuated), the data interface 202 is conditioned to automatically compile and print the Procedure Report 310 and Event Report 312 at the end of the procedure.

D. The Data Exchange task

I. Data Transfer Function

It should be appreciated that, due to the features of the PROCEDURE DRIVER task module 222, the FILE SYSTEM task module 224, the PRINT task module, and the USER INTERFACE task module 230 already described, the data interface 202 is fully integrated to store, retrieve, and manipulate data without the use of or connection to an external computer 206.

However, the second port 210 makes it possible, if desired, to link the data interface 202 to an external computer 206. The DATA EXCHANGE task module 228 includes a data share function 384, which establishes a communication exchange interface between the on-board data interface 202 and the external computer 206.

In one embodiment, the external computer 206 coupled to the second port link 210 can include its own resident control software 338 (see FIG. 7). The software 338 is programmed to prompt the data interface 202 for key control and processing parameters of a given procedure. The data share function 384 of the DATA EXCHANGE task module 228 responds by assembling and downloading this data to the computer 206 for storage, retrieval, or manipulation.

In this arrangement, the data share function 384 of the DATA EXCHANGE task module 228 generates a random access data file 340, designated Act2_Proc_Data in FIG. 7. Act2_Proc_Data file 340 is formatted the same as the Act_Proc_Data file 234 maintained in random access memory by the PROCEDURE DRIVER task module 222. While a given procedure is underway, the data share function 384 periodically copies data from the Act_Proc_Data file 234 into the Act2_Proc_Data file 340. While a given procedure is underway, the data share function 384 can also periodically read event data residing in the current event data file space 250 on the storage device 204. However, while a given procedure is underway, the data share function 384 can not read the current procedure data file space 248 on the storage device 204.

The control software 338 residing in the external computer 206 sends programmed ASCII input to the data share function 384 as the procedure progresses. In response to the programmed input, the data share function 384 builds desired responses based upon data read from the Act2_Proc_Data file 340 or from the current event data file space 250 on the storage device 204. The data share function 384 transmits the responses to the external computer 206 for storage, retrieval, or manipulation. Once a procedure is completed, the data share function 384 can read data from both the procedure data file space 248 and the event data file space 250 on the storage device 204, to build responses to preprogrammed input from the external computer 206.

In the illustrated embodiment, the data share function 384 is automatically activated whenever the COMMUNICATION MANAGER task module 218 senses communication through the port 210 with a computer 206 having the enabling control software 338.

ii. Control Input Function

The DATA EXCHANGE task module 228 also includes a data control function 386, by which process control input 388 can be received from the external computer 206. In this arrangement, the control software 338 of the computer 206 establishes on the computer 206 a graphical user interface compatible with the interface manager 66. The data control function 386 transmits the process control input 388 from computer 206 to the interface manager 66, via the USER INTERFACE task module 230. The process control input 388 serves the same command and control functions as corresponding input from the screen 60, as previously described.

The data control function 386 makes it possible to establish or alter processing parameters for the controller 18 from a remote location.

iii. Purge Function

In the illustrated embodiment, the DATA EXCHANGE task module 228 includes a PURGE function 344. The PURGE function 344 performs house-keeping on the number of files managed by the FILE SYSTEM task module 224. At prescribed intervals (e.g., at the conclusion or each procedure), the PURGE function 344 reads the metadata file nodes 260/262 maintained by the FILE SYSTEM task module 224. The PURGE function directs the FILE SYSTEM task module 224 to delete data from the procedure and event data file spaces in excess of a prescribed number according to where the oldest data exists. For example, if the FILE SYSTEM task module 224 has allocated file space for forty (40) procedures (i.e., forty procedure data file spaces and forty event data file spaces), the PURGE function 314 deletes the data in allocated procedure and event file spaces in excess of thirty (30) each, according to where the oldest data are stored. In this way, the data interface 202 maintains current procedure and event data 236 and 238 for the thirty (30) most recent procedures. The ringfile nature of the system condition data 336 and dump sensor data 350 automatically assures that only recent data is maintained.

In a representative implementation, the storage device 204 has eight megabytes of storage space. The block device function 240 allocates two files spaces of 100 kilobytes each, one for the system condition data file space 252 and the other being an open extra file space. The block device function 240 also allocates two files spaces of 1 megabyte each, one for the dump sensor data file space 254 and the other being an open extra file space. The block device function 240 further allocates 70 file spaces of 5.6 kilobytes each as procedure data file spaces 248, and 70 file spaces of 66.5 kilobytes each as event data file spaces 250. Controlled by the PURGE function 314, thirty each of these file spaces 248 and 250 hold the current procedure data. The remaining thirty are free file spaces.

E. The User Interface Task (Data Exchange Task Support)

i. File Transfer Function

In another embodiment, procedure or event data files residing on the storage device 204 can be transferred, or downloaded, in any arbitrary order to any compatible external computer 206 linked to the second port, as controlled by the USER INTERFACE task module 230 of the data interface 202, and without otherwise requiring control software on the external computer 206.

As implemented in the illustrated embodiment, the File Directory Submenu (see FIG. 13) includes a TRANSFER push button field 346. When the TRANSFER button field 346 is pushed, the USER INTERFACE task module 230 commands the FILE SYSTEM task module 224 to copy data in the highlighted file from the storage device 204 to the DATA EXCHANGE task module 228. The DATA EXCHANGE task module 228, in turn, transfers the data to the external computer 206 via the second port. The external computer 206 can store, retrieve, and manipulate the data using onboard data processing software.

The integrated data recording function of the data interface 202 does not require an external computer 206 connected during the data storage process. Furthermore, any external computer 206 may be connected after the data has been stored by the data interface 202. The data interface 202 also makes possible to download data to an external computer 206 at an arbitrary time and in an arbitrary fashion after the processing function has been completed. Data collected by the data interface 202 is also available to field service personnel, which allows accurate program diagnosis and instrument performance evaluation.

ii. File Import Function

Figure 21:
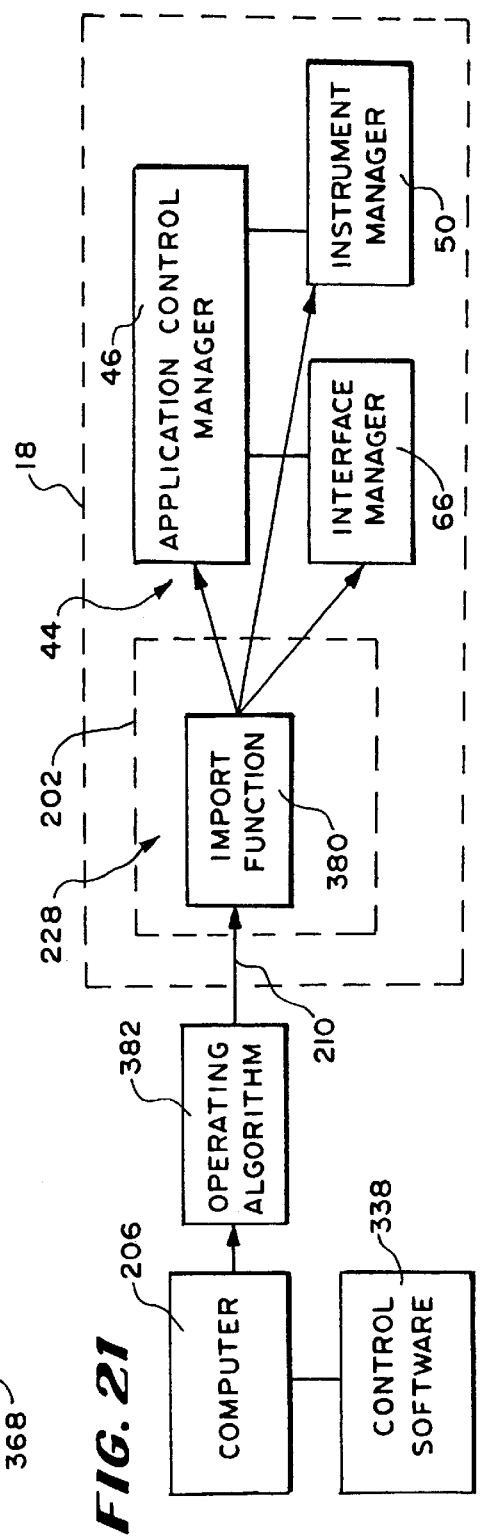
FIG. 21 is a schematic view of the import configuration function of the data interface.

In the illustrated embodiment (see FIG. 21), the DATA EXCHANGE task module 228 includes an import function 380. The import function 380 permits the import, or uploading, of additional operating algorithms 382 from the external computer 206 into the controller 18 for implementation.

In the illustrated implementation, the System Configuration Submenu (FIG. 18) includes a IMPORT CONFIGURATION button 378, which, when pushed, activates an import function 380. The import function 380 boots the MPU 44 of the controller 18 into an import mode, which is governed by the control software 338 of the computer 206 coupled to the port link 210. Governed by input from the computer 206, the control software 338 installs one or more additional operating algorithms 382 as process software in EPROM's in the MPU 44, and, in particular, the instrument control manager 46, the instrument manager 50, and the interface manager 66.

The imported algorithms 382 establish one or more new applications that can be called up by the application control manager 46. The imported algorithms also install implementing process software in the instrument manager 50 and interface manager 66.

F. The Data Dump Task

In the illustrated embodiment, the user interface 202 also includes a DATA DUMP task module 366. The DATA DUMP task module 366 communicates with the port link 348 and the FILE SYSTEM task module 224. The DATA DUMP task function 366 periodically reads the data contents of the file space (i.e., space 254 in FIG. 8), where the FILE SYSTEM task module 244 writes the dump sensor data 350. The DATA DUMP task module 366 formats the current dump sensor data 350 as a message buffer output 370, which is transmitted through the port link 348 to a connected external computer 206'.

The external computer 206' includes enabling control software 368. The software 368 conditions the computer 206' to receive the formatted message buffer output 370 for storage, retrieval, or manipulation.

For example, the DATA DUMP task module 366 can automatically assemble and transmit a message buffer output 370 every five seconds to the port link 348, for download to the external computer 206'. This time-sequential record, maintained by the external computer 206' provides an accurate, comprehensive account of sensed conditions throughout the procedure. This record can be used by service or diagnostic technicians to troubleshoot system errors. This record can also aid research and development technicians in designing, developing, and implementing new operating algorithms for the application control manager 46.

In FIG. 20, the DATA DUMP task module 366 includes a predictor function 372. The predictor function 372 includes algorithms which analyze the contents of successive message buffer outputs 370 according to predetermined criteria. For example, the criteria can gauge sensed conditions with respect to compliance with established operating ranges. The criteria can assess changes in sensed conditions over time, using proportional, integral, or derivative analyses, or combinations thereof. The criteria can compare the sensed conditions with respect to other empirically developed standards or test algorithms, using, for example, correlation or fuzzy logic techniques.

On the basis of its analyses, the predictor function 372 generates diagnostic output files 374. The diagnostic output files 374 indicate system performance trends and predict potential system errors or failures before they occur.

The output files 374 are managed by the FILE SYSTEM task module 224 in the same manner as, for example, the system condition data files 336, for viewing through the USER INTERFACE task module 230 with the system condition data files 336. FIG. 17 shows the inclusion of a diagnostic notice 376 based upon a diagnostic output file 374, which identifies an adverse performance trend and recommends a service check before failure occurs. Alternatively, or in combination, the contents of a diagnostic output file 374 could be included as an item in the Event Report 312, handled through the REPORT task module 226.

Alternatively, or in combination, the enabling control software 368 of the external computer 206' can incorporate the predictor function 372. In this arrangement, the external computer 206' can provide its own diagnostic notice 376 in visual or hard copy form.

The data interface 202 and graphical interface as described can be realized, e.g., as a "C" language program implemented using the MS WINDOWS™ application and the standard WINDOWS 32 API controls, e.g., as provided by the WINDOWS™ Development Kit, along with conventional graphics software disclosed in public literature.

Various features of the invention are set forth in the following claims.

What is claimed is:

1. A blood processing system comprising
a device including processing hardware to carry out a blood processing procedure,
a processing manager residing on the device to monitor status conditions during the blood processing procedure, and
a data interface residing on the device including a data generator task to generate data based upon monitored status conditions, a flash memory data storage medium including a block file space having a fixed maximum size, and a file manager task to write the data to the block file space of the flash memory data storage medium.

2. A system according to claim 1
wherein the file manager task overwrites old data in the block file space with new data.

3. A system according to claim 1
wherein the file manager task appends the data to the block file space until the fixed maximum size is reached.

4. A system according to claim 3
wherein the file manager task generates an output when the fixed maximum size is reached.

5. A system according to claim 1
wherein, when the fixed maximum size is exceeded, the file manager task appends the data to the block file space by overwriting oldest data with newest data.

6. A system according to claim 1
wherein the data interface includes a print task coupled to the file manager task to print data written to the flash memory storage medium.

7. A system according to claim 1
wherein the data interface includes a view task coupled to the file manager task to view data written to the flash memory storage medium.

8. A system according to claim 1
wherein the data interface includes an exchange task coupled to the file manager task to offload data from the flash memory storage medium.

9. A system according to claim 1
wherein the data interface includes a system task coupled to the file manager task for manipulating data written to the flash memory storage medium.

10. A system according to claim 1 wherein the block file space includes a node to record metadata for the block file space.

11. A system according to claim 10
wherein the data interface includes a system task for viewing the metadata.

12. A blood processing system comprising
means for monitoring status conditions over time during a blood processing procedure,
means for generating data based upon monitored status conditions,
a flash memory storage medium including a block file space having a fixed maximum size, and
means for writing the data to [a] the block file space of the flash memory storage medium.

13. A system according to claim 12
and further including means for manipulating the data written to the flash memory storage medium.

14. A system according to claim 12
and further including means for retrieving the data written to the flash memory storage medium.

15. A blood processing system comprising
a device including processing hardware to carry out a blood processing procedure,
a processing control manager residing on the device to monitor status conditions during the blood processing procedure, a data interface residing on the device including
  a data storage medium having first and second block file spaces to receive data,
  a data generator task to generate discrete first and second data streams based upon status conditions monitored over time, and
  a file manager task to append each first data stream chronologically to the first block file space and to overwrite each second data stream in succession in the second block file space.

16. A system according to claim 15 wherein the data interface includes a print task element coupled to the file manager task to compile data in at least one of the block files for printing.

17. A system according to claim 16 wherein the print task formats the complied data for printing as a prescribed report.

18. A system according to claim 15 wherein the data interface includes a view task coupled to the file manager task to compile data in at least one of the block files for viewing.

19. A system according to claim 15 wherein the data interface includes an exchange task coupled to the file manager task to offload data from at least one of the block files.

20. A system according to claim 15 wherein the data interface includes a system task coupled to the file manager task for manipulating data written to at least one of the block files.

21. A system according to claim 15 wherein the first block file has a fixed maximum size, and wherein the file manager task appends the first data streams chronologically to the first block file space until the fixed maximum size is reached.

22. A system according to claim 21 wherein the file manager task generates an output when the fixed maximum size is reached.

23. A system according to claim 15 wherein the first block file has a fixed maximum size, and wherein, when the fixed maximum size is exceeded, the file manager task appends by overwriting oldest first data streams with newest first data streams.

24. A system according to claim 15 wherein both the first and second block file spaces have fixed maximum sizes.

25. A system according to claim 15 wherein the data storage medium comprises a flash memory storage device.

26. A blood processing system comprising
a device including processing hardware to carry out a blood processing procedure,
a processing control manager on the device coupled to the processing hardware to monitor status conditions over time during the blood processing procedure, and
a data interface on the device coupled to the processing control manager including
  a data storage medium including a file space formatted to a fixed maximum size,
  a data generator task to generate chronologic data streams based upon status conditions monitored over time, and
  a file manager task to append the chronologic data streams to the file space in chronologic order and to read the chronologic data streams from the file space as a chronologic block file.

27. A system according to claim 26 wherein the data interface includes a print task coupled to the file manager task to compile data in the chronologic block file for printing.

28. A system according to claim 26 wherein the data interface includes a view task coupled to the file manager task to compile data in the chronologic block file for viewing.

29. A system according to claim 26 wherein the file manager task appends chronologic data streams to the file space until the fixed maximum size is reached.

30. A system according to claim 29 wherein the file manager task generates an output when the fixed maximum size is reached.

31. A system according to claim 26 wherein the file manager task appends chronologic data streams to the file space by overwriting oldest data streams with newest data streams.

32. A system according to claim 26 wherein the data storage medium comprises a flash memory storage device.

33. A blood processing system comprising
a device including processing hardware to carry out a blood processing procedure,
a processing control manager on the device coupled to the processing hardware to monitor status conditions over time during the blood processing procedure, and
a data interface on the device coupled to the processing control manager including
  a data storage medium including a file space formatted to a fixed maximum size,
  a data generator task to generate a time-specific data stream based upon status conditions at a point in time, and
  a file manager task to write the time-specific data stream to the file space as a time-specific block file and to read the time-specific data stream from the file space as the time-specific block file.

34. A system according to claim 33 wherein the data interface includes a print task coupled to the file manager task to compile data in the time-specific block file for printing.

35. A system according to claim 33 wherein the data storage medium comprises a flash memory storage device.

36. A blood processing system comprising
a device including processing hardware to carry out a blood processing procedure,
a processing control manager on the device coupled to the processing hardware to monitor status conditions over time during the blood processing procedure, and
a data interface on the device coupled to the processing control manager including
  a data storage medium including a first file space formatted to a fixed maximum size and a second file space formatted to a fixed maximum size,
  a data generator task to generate chronologic data streams based upon status conditions monitored over time and to generate a time-specific data stream, based upon status conditions at a point in time, and
  a file manager task to append the chronologic data streams in chronologic order to the first file space and not the second file space and to write the time-specific data stream to the second file space and not the first file space as a time-specific block file.

37. A system according to claim 36
wherein the data storage medium comprises a flash memory storage device.

38. A method for processing data during a blood processing procedure comprising the steps of
monitoring status conditions over time during the blood processing procedure,
generating data based upon monitored status conditions,
providing a flash memory storage medium including a block file space having a fixed maximum size, and
writing the data to the block file space of the flash memory storage medium.

39. A method according to claim 38
and further including the step of manipulating the data written to the flash memory storage medium.

40. A method according to claim 38
and further including the step of retrieving the data written to the flash memory storage medium.

41. A method for processing data during a blood processing procedure comprising the steps of
monitoring status conditions over time during the blood processing procedure,
generating a succession of first and second data streams based upon monitored status conditions, and
writing the first and second data streams to a storage medium having allocated first and second block file spaces, by appending each first data stream in chronological order only to the first block file space and by overwriting each second data stream in succession only to the second block file space, to thereby maintain during the procedure a chronologic block file in the first block file space and a time-specific block file in the second block file space.

42. A method according to claim 41
and further including the step of manipulating the data written to at least one of the block file spaces.

43. A method according to claim 41
and further including the step of retrieving the data written to at least one of the block file spaces.

44. A method according to claim 41
wherein the writing step includes writing the first and second data streams to a flash memory storage medium.

* * * * *